United States Patent

Bereznak et al.

[11] Patent Number: 5,945,423
[45] Date of Patent: *Aug. 31, 1999

[54] FUNGICIDAL FUSED BICYCLIC PYRIMIDINONES

[75] Inventors: James Francis Bereznak, Aston, Pa.; Zen-Yu Chang, Hockessin, Del.; Thomas Paul Selby; Charlene Gross Sternberg, both of Wilmington, Del.

[73] Assignee: E. I. du Pont de Nemours and Company, Wilmington, Del.

[ * ] Notice: This patent is subject to a terminal disclaimer.

[21] Appl. No.: 09/007,336

[22] Filed: Jan. 14, 1998

Related U.S. Application Data

[63] Continuation of application No. 08/545,827, filed as application No. PCT/US94/04965, May 10, 1994, Pat. No. 5,747,497, which is a continuation-in-part of application No. 08/144,904, Oct. 28, 1993, abandoned, and a continuation-in-part of application No. 08/060,629, May 12, 1993, abandoned.

[51] Int. Cl.$^6$ .................... C07D 239/72; A01N 43/54
[52] U.S. Cl. .................... 514/259; 514/260; 514/257; 514/211; 514/220; 514/63; 514/183; 514/224.5; 514/229.8; 540/548; 540/559; 540/468; 540/471; 544/229; 544/250; 544/284; 544/285; 544/287; 544/288
[58] Field of Search .................... 544/229, 283–293; 514/259–60, 260, 257, 63, 229.8; 504/240, 193; 540/548, 468

[56] References Cited

U.S. PATENT DOCUMENTS

| | | | |
|---|---|---|---|
| 3,755,582 | 8/1973 | Bullock et al. | 424/251 |
| 3,867,384 | 2/1975 | Bullock et al. | 260/256.4 |
| 4,521,420 | 6/1985 | Maurer et al. | 514/259 |
| 5,276,038 | 1/1994 | Takasugi et al. | 514/259 |
| 5,304,530 | 4/1994 | Cliff et al. | 504/266 |
| 5,354,755 | 10/1994 | Takasugi et al. | 514/259 |
| 5,747,497 | 5/1998 | Bereznak et al. | 514/259 |

FOREIGN PATENT DOCUMENTS 2218301 10/1973 Germany.

Primary Examiner—John M. Ford

[57] ABSTRACT

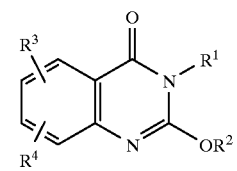

(I)

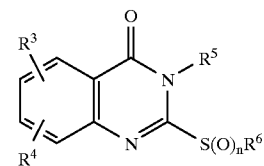

(II)

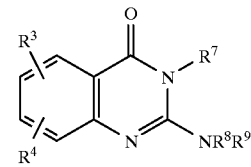

(III)

This invention pertains to compounds of Formulae (I), (II), and (III) including all geometric and stereoisomers, N-oxides, agriculturally-suitable salts thereof, agricultural compositions containing them and their use as fungicides, wherein: Q is O or S; and n, $R^1$, $R^2$, $R^3$, $R^4$, $R^5$, $R^6$, $R^7$, $R^8$, and $R^9$ are described in the text.

10 Claims, No Drawings

FUNGICIDAL FUSED BICYCLIC PYRIMIDINONES

This application is a continuation of U.S. patent application Ser. No. 08/545,827, now U.S. Pat. No. 5,747,497, filed Nov. 8, 1995, the national filing under 35 USC 371 of International Application No. PCT/US94/04965 filed May 10, 1994, which is a CIP of U.S. patent application Ser. No. 08/144,904, now abandoned, filed Oct. 28, 1993, and a CIP of U.S. patent application Ser. No. 08/060,629 filed May 12, 1993, now abandoned.

This invention relates to certain 4(3H)-quinazolinones, their agriculturally suitable salts and compositions, and methods of their use as general or selective fungicides, in particular for the control of cereal powdery mildew both preventive and curative.

U.S. Pat. No. 3,755,582 and U.S. Pat. No. 3,867,384 disclose certain 4(3H)-quinazolinone fungicides. These patents, however, do not specifically disclose the compounds of the present invention.

SUMMARY OF THE INVENTION

This invention comprises compounds of Formulae I, II, and III including all geometric and stereoisomers, N-oxides, agriculturally-suitable salts thereof, agricultural compositions containing them and their use as fungicides:

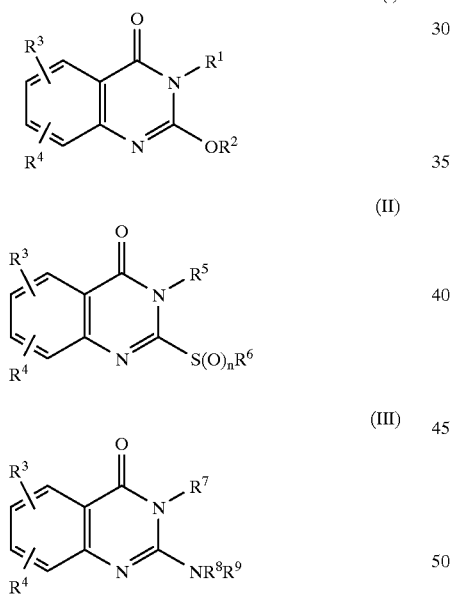

wherein:

n is 0, 1 or 2;

Q is independently O or S;

$R^1$ is $C_3$–$C_{10}$ alkyl; $C_3$–$C_5$ cycloalkyl; $C_4$–$C_{10}$ alkenyl; $C_4$–$C_{10}$ alkynyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_5$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$, nitro, cyano, or phenyl optionally substituted with $R^{14}$, $R^{15}$, and $R^{16}$; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{11}R^{12}$; or pyridyl, furanyl, thienyl, naphthyl, benzofuranyl, benzothienyl, or quinolinyl each optionally substituted with $R^{14}$, $R^{15}$, and $R^{16}$;

$R^2$ is $C_3$–$C_{10}$ alkyl; $C_6$–$C_7$ cycloalkyl; $C_3$–$C_{10}$ alkenyl, $C_3$–$C_{10}$ alkenyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_3$–$C_{10}$ cyanoalkyl; $C_2$–$C_{10}$ nitroalkyl; $C_1$–$C_{10}$ alkyl substituted with $CO_2R^{11}$, $NR^{11}R^{12}$, or phenyl optionally substituted with $R^{13}$, $R^{15}$, and $R^{16}$; phenyl optionally substituted with $R^{13}$, $R^{15}$, and $R^{16}$; —N=$CR^{11}R^{11}$; or —$NR^{11}R^{12}$; or $R^1$ and $R^2$ are taken together to form —$CH_2(CH_2)_m$ $CH_2$—;

m is 1–4;

$R^3$ is halogen; $C_1$–$C_8$ alkyl; $C_3$–$C_8$ cycloalkyl; $C_2$–$C_8$ alkenyl; $C_2$–$C_8$ alkynyl; $C_1$–$C_8$ haloalkyl; $C_3$–$C_8$ haloalkenyl; $C_3$–$C_8$ haloalkynyl; $C_1$–$C_8$ alkoxy; $C_1$–$C_8$ haloalkoxy; $C_3$–$C_8$ alkenyloxy; $C_3$–$C_8$ alkynyloxy; $C_1$–$C_8$ alkylthio; $C_3$–$C_8$ alkenylthio; $C_3$–$C_8$ alkynylthio; $C_1$–$C_8$ alkylsulfinyl; $C_1$–$C_8$ alkylsulfonyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ cycloalkylalkyl; $C_3$–$C_8$ trialkylsilyl; nitro; $NR^{11}R^{12}$; $C_5$–$C_8$ trialkylsilylalkynyl; or phenyl optionally substituted with at least one $R^{13}$;

$R^4$ is hydrogen; halogen; $C_1$–$C_4$ alkyl; $C_1$–$C_4$ haloalkyl; $C_1$–$C_4$ alkoxy; or $C_1$–$C_4$ haloalkoxy;

$R^5$ is $C_3$–$C_5$ alkyl; $C_7$–$C_{10}$ alkyl; $C_4$–$C_7$ alkenyl; $C_3$–$C_5$ alkynyl; $C_1$–$C_{10}$ haloalkyl; $C_5$–$C_{10}$ haloalkenyl; $C_3$–$C_{10}$ haloalkynyl; $C_2$–$C_{10}$ alkoxyalkyl other than methoxypropyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$, nitro, or phenyl optionally substituted with at least one of $R^{14}$, $R^{15}$, and $R^{16}$; $C_2$–$C_{10}$ alkyl substituted with cyano; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{11}R^{12}$; or phenyl, furanyl, thienyl, naphthyl, benzofuranyl, or benzothienyl each optionally substituted with $R^{14}$, $R^{15}$, and $R^{16}$;

$R^6$ is $C_3$–$C_{10}$ alkyl; $C_3$–$C_7$ alkenyl; $C_3$–$C_{10}$ alkynyl; $C_1$–$C_{10}$ haloalkyl; $C_3$–$C_{10}$ haloalkenyl; $C_3$–$C_{10}$ haloalkynyl; $C_3$–$C_{10}$ alkoxyalkyl other than propoxymethyl; $C_2$–$C_{10}$ alkylthioalkyl, $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl, $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_5$–$C_{10}$ cyanoalkyl; $C_2$–$C_{10}$ nitroalkyl; or $C_3$–$C_{10}$ alkyl substituted with $CO_2R^{11}$, $NR^{11}R^{12}$, or phenyl optionally substituted with $R^{13}$, $R^{15}$, and $R^{16}$; or phenyl optionally substituted with $R^{13}$, $R^{15}$, and $R^{16}$; or $R^5$ and $R^6$ are taken together to form —$CH_2(CH_2)_m$ $CH_2$—;

$R^7$ is $C_3$–$C_{10}$ alkyl; $C_3$–$C_7$ cycloalkyl; $C_4$–$C_7$ alkenyl; propynyl; $C_5$–$C_{10}$ alkynyl; $C_2$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$ or nitro; $C_2$–$C_{10}$ alkyl substituted with cyano; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{12}R_{17}$; or phenyl, pyridyl, furanyl, thienyl, naphthyl, benzofuranyl, benzothienyl, or quinolinyl each optionally substituted with $R^{14}$, $R^{15}$, and $R^{16}$;

$R^8$ is hydrogen; $C_1$–$C_4$ alkyl; or —$C(=O)R^{10}$;

$R^9$ is hydrogen; $C_2$–$C_{10}$ alkyl; $C_3$–$C_7$ cycloalkyl; $C_3$–$C_{10}$ alkenyl; $C_3$–$C_{10}$ alkynyl; $C_3$–$C_{10}$ haloalkyl; $C_3$–$C_{10}$ haloalkenyl; $C_3$–$C_{10}$ haloalkynyl; $C_3$–$C_{10}$ alkoxyalkyl other than butoxyethyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$; $C_4$–$C_{10}$ cyanoalkyl; $C_2$–$C_{10}$ nitroalkyl; $C_1$–$C_8$ alkyl substituted with $CO_2R^{11}$; pyridyl, furanyl, thienyl, or naphthyl each optionally substituted with $R^{14}$, $R^{15}$, and $R^{16}$, —$N=CR^{11}R^{11}$; —$NR^{12}R^{17}$; —$OR^{12}$; or —$NC(=Q)NR^{11}R^{12}$; or $R^3$ and $R^4$ are both iodine and $R^9$ is phenyl optionally substituted with $R^{14}$, $R^{15}$, and $R^{16}$; or $R^7$ and $R^9$ are taken together to form —$CH_2(CH_2)_m$ $CH_2$—;

$R^{10}$ is hydrogen; $C_1$–$C_4$ alkyl; $C_1$–$C_4$ alkoxy; or $NR^{11}R^{12}$;

$R^{11}$ is independently hydrogen; $C_1$–$C_4$ alkyl; or phenyl optionally substituted with at least one $R^{13}$;

$R^{12}$ is independently hydrogen; $C_1$–$C_8$ alkyl; or phenyl optionally substituted with at least one $R^{13}$; or $R^{11}$ and $R^{12}$ are taken together to form —$CH_2CH_2CH_2CH_2$—, —$CH_2(CH_2)_3CH_2$—, —$CH_2CH_2OCH_2CH_2$—, —$CH_2CH(Me)CH_2CH(Me)CH_2$—, or —$CH_2CH(Me)OCH(Me)CH_2$—;

$R^{13}$ is independently halogen; $C_1$–$C_4$ alkyl; $C_1$–$C_4$ alkoxy; $C_1$–$C_4$ haloalkyl; nitro; or cyano;

$R^{14}$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R^{13}$; cyano; nitro; $C_1$–$C_6$ haloalkoxy; $C_1$–$C_6$ haloalkylthio; $C_2$–$C_6$ alkenyl; $C_2$–$C_6$ haloalkenyl; acetyl; $CO_2Me$; or $N(C_1$–$C_2$ alkyl$)_2$;

$R^{15}$ is independently methyl; ethyl; methoxy; methylthio; halogen; or trifluoromethyl;

$R^{16}$ is independently halogen; and $R^{17}$ is independently $C_1$–$C_8$ alkyl; or phenyl optionally substituted with at least one $R^{13}$.

DETAILED DESCRIPTION OF THE INVENTION

In the above recitations, the term "alkyl", used either alone or in compound words such as "alkylthio," "haloalkyl," or "alkylthioalkyl" denotes straight-chain or branched alkyl; e.g., methyl, ethyl, n-propyl, i-propyl, or the different butyl, pentyl, hexyl, etc. isomers.

"Cycloalkyl" denotes cyclopropyl, cyclobutyl, cyclopentyl, and cyclohexyl. The term "cycloalkyloxyalkyl" denotes the cycloalkyl groups linked through an oxygen atom to an alkyl chain. Examples include cyclopentyloxymethyl and cyclohexyloxybutyl. The term "cycloalkylthioalkyl" are the cycloalkyl groups linked through a sulfur atom to an alkyl chain; e.g., cyclopropylthiopentyl. "Cycloalkylalkyl" denotes a cycloalkyl ring attached to a branched or straight-chain alkyl; e.g. cyclopropylmethyl and cyclohexylbutyl.

"Alkenyl" denotes straight chain or branched alkenes; e.g., 1-propenyl, 2-propenyl, 3-propenyl and the different butenyl, pentenyl, hexenyl, etc. isomers. Alkenyl also denotes polyenes such as 1,3-hexadiene and 2,4,6-heptatriene.

"Alkynyl" denotes straight chain or branched alkynes; e.g., ethynyl, 1-propynyl, 3-propynyl and the different butynyl, pentynyl, hexynyl, etc. isomers. "Alkynyl" can also denote moieties comprised of multiple triple bonds; e.g., 2,7-octadiyne and 2,5,8-decatriyne.

"Alkoxy" denotes methoxy, ethoxy, n-propyloxy, isopropyloxy and the different butoxy, pentoxy, hexyloxy, etc. isomers. "Alkoxyalkenyl" and "alkoxyalkynyl" denoted groups in which the alkoxy group is bonded throught the oxygen atom to an alkenyl or alkynyl group, respectively. Examples include $CH_3OCH_2CH=CH$ and $(CH_3)_2CHOCH_2C\equiv CCH_2$. The corresponding sulfur derivatives are denoted "alkylthioalkenyl" and "alkylthioalkynyl." Examples of the former include $CH_3SCH_2CH=CH$ and $CH_3CH_2SCH_2(CH_3)CH=CHCH_2$, and an example of the latter is $CH_3CH_2CH_2CH_2SCH_2C\equiv C$.

"Alkenyloxy" denotes straight chain or branched alkenyloxy moieties. Examples of alkenyloxy include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkenylthio" denotes the similar groups wherein the oxygen atom is replaced with a sulfur atom; e.g., $H_2C=CHCH_2S$ and $(CH_3)CH=C(CH_3)CH_2S$. The term "alkenyloxyalkyl" denotes groups in which the alkenyloxy moiety is attached to an alkyl group. Examples include $H_2C=CHCH_2OCH_2CH_2$, $H_2C=CHCH_2OCH(CH_3)CH_2$, etc. "Alkenylthioalkyl" denotes the alkenylthio moieties bonded to an alkyl group. Examples include $H_2C=CHCH_2SCH(CH_3)CH(CH_3)$ and $(CH_3)CH=C(CH_3)CH_2SCH_2$.

"Alkynyloxy" denotes straight or branched alkynyloxy moieties. Examples include $HC\equiv CCH_2O$, $CH_3C\equiv CCH_2O$ and $CH_3C\equiv CCH_2CH_2O$. "Alkynyloxyalkyl" denotes alkynyloxy moieties bonded to alkyl groups; e.g., $CH_3C{\equiv}CCH_2OCH_2CH_2$ and $HC{\equiv}CCH_2OCH(CH_3)CH_2$. "Alkynylthioalkyl" denotes alkynylthio moieties bonded to alkyl groups. Example include $CH_3C{\equiv}CCH_2SCH_2CH_2$ and $CH_3C{\equiv}CCH_2CH_2SCH(CH_3)CH_2$.

"Alkylthio" denotes methylthio, ethylthio, and the different propylthio, butylthio, pentylthio and hexylthio isomers. "Alkylthioalkyl" denotes alkylthio groups attached to an alkyl chain; e.g., $CH_3CH_2SCH_2CH(CH_3)$ and $(CH_3)_2CHSCH_2$.

"Alkylsulfinyl" denotes both enantiomers of an alkylsulfinyl group. For example, $CH_3S(O)$, $CH_3CH_2S(O)$, $CH_3CH_2CH_2S(O)$, $(CH_3)_2CHS(O)$ and the different butylsulfinyl, pentylsulfinyl and hexylsufinyl isomers. "Alkylsulfinylalkyl" denotes alkylsulfinyl groups attached to an alkyl chain; e.g., $CH_3CH_2S(O)CH_2CH(CH_3)$ and $(CH_3)_2CHS(O)CH_2$.

Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylsulfonylalkyl" denotes alkylsulfonyl groups attached to an alkyl chain; e.g., $CH_3CH_2S(O)_2CH_2CH(CH_3)$ and $(CH_3)_2CHS(O)_2CH_2$.

The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CF_2$. Examples of "haloalkenyl" include $(Cl)_2C{=}CHCH_2$ and $CF_3CH_2CH{=}CHCH_2$. "Haloalkenyloxyalkyl" denotes haloalkenyl groups bonded to oxygen and in turn bonded to alkyl groups. Examples include $CF_3CH_2CH{=}CHCH_2OCH_2$ and $(Cl)_2C{=}CHCH_2OCH_2CH_2$. Examples of "haloalkynyl" include $HC{\equiv}CCHCl$, $CF_3C{\equiv}C$, $CCl_3C{\equiv}C$ and $FCH_2C{\equiv}CCH_2$. "Haloalkynyloxyalkyl" denotes haloalkynyl groups bonded through an oxygen atom to an alkyl moiety. Examples include $CF_3C{\equiv}CCH_2OCH_2CH_2$, $ClCH_2C{\equiv}CCH_2CH_2OCH(CH_3)$, etc. Examples of "haloalkoxy" include $CF_3O$, $CCl_3CH_2O$, $CF_2HCH_2CH_2O$ and $CF_3CH_2O$. "Haloalkoxyalkyl" denotes haloalkoxy groups bonded to straight-chain or branched alkyl groups; e.g., $CF_2HCH_2CH_2OCH_2CH_2$, $CCl_3CH_2OCH(CH_3)$ and $CF_3OCH_2$.

"Trialkylsilyl" designates a group with three alkyl groups bonded to silicon; e.g., $(CH_3)_3Si$ and $t\text{-}Bu(CH_3)_2Si$. "Trialkylsilylalkyl" denotes trialkylsilyl groups bonded to another straight-chain or branched alkyl group. Examples include $(CH_3)_3SiCH_2$ and $t\text{-}Bu(CH_3)_2SiCH_2CH(CH_3)CH_2$.

The total number of carbon atoms in a substituent group is indicated by the "$C_i$–$C_j$" prefix where i and j are numbers from 1 to 10. For example, $C_1$–$C_3$ alkylsulfonyl designates methylsulfonyl through propylsulfonyl; $C_2$ alkoxyalkoxy designates $CH_3OCH_2O$; $C_3$ alkoxyalkoxy designates, for example, $CH_3OCH_2CH_2O$ or $CH_3CH_2OCH_2O$; and $C_4$ alkoxyalkoxy designates the various isomers of an alkoxy group substituted with a second alkoxy group containing a total of 4 carbon atoms, examples including $CH_3CH_2CH_2OCH_2O$, and $CH_3CH_2OCH_2CH_2O$. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

Preferred for reasons of ease of synthesis or greater fungicidal activity are:

Preferred 1. The compounds of Formula I as defined above wherein:

Q is O;

$R^1$ is $C_3$–$C_8$ alkyl; $C_4$–$C_8$ alkenyl; $C_4$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_5$–$C_8$ cycloalkylalkyl: $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or pyridyl, furanyl, or thienyl each optionally substituted with $R^{14}$ and $R^{15}$;

$R^2$ is $C_3$–$C_8$ alkyl; $C_3$–$C_8$ alkenyl; $C_3$–$C_8$ alkynyl; $C_1$–$C_8$ haloalkyl; $C_3$–$C_8$ haloalkenyl; $C_3$–$C_8$ alkoxyalkyl; $C_2$–$C_8$ alkylthioalkyl; $C_4$–$C_8$ cycloalkylalkyl; $C_3$–$C_8$ cyanoalkyl; $C_4$–$C_8$ alkenyloxyalkyl; or phenyl optionally substituted with $R^{13}$;

$R^3$ is halogen; $C_1$–$C_8$ alkyl; $C_2$–$C_8$ alkynyl; $C_3$–$C_8$ cycloalkyl; $C_1$–$C_8$ haloalkyl; $C_1$–$C_8$ alkoxy; $C_1$–$C_8$ haloalkoxy; $C_1$–$C_8$ alkylthio; $C_1$–$C_8$ alkylsulfonyl; $C_2$–$C_8$ alkoxyalkyl; $C_2$–$C_8$ alkylthioalkyl; $C_4$–$C_8$ cycloalkylalkyl; or $C_5$–$C_8$ trialkylsilylalkynyl; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

Preferred 2. The compounds of Formula II as defined above wherein:

Q is O;

n is 0;

$R^3$ is halogen; $C_1$–$C_8$ alkyl; $C_2$–$C_8$ alkynyl; $C_3$–$C_8$ cycloalkyl; $C_1$–$C_8$ haloalkyl; $C_1$–$C_8$ alkoxy; $C_1$–$C_8$ haloalkoxy; $C_1$–$C_8$ alkylthio; $C_1$–$C_8$ alkylsulfonyl; $C_2$–$C_8$ alkoxyalkyl; $C_2$–$C_8$ alkylthioalkyl; $C_4$–$C_8$ cycloalkylalkyl; or $C_5$–$C_8$ trialkylsilylalkynyl;

$R^5$ is $C_3$–$C_5$ alkyl; $C_4$–$C_7$ alkenyl; $C_3$–$C_5$ alkynyl; $C_1$–$C_8$ haloalkyl; $C_5$–$C_8$ haloalkenyl; $C_2$–$C_8$ alkoxyalkyl other than methoxypropyl; $C_2$–$C_8$ alkylthioalkyl; $C_4$–$C_8$ cycloalkylalkyl; $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or phenyl, furanyl, or thienyl each optionally substituted with $R^{14}$ and $R^{15}$;

$R^6$ is $C_3$–$C_8$ alkyl; $C_3$–$C_7$ alkenyl; $C_3$–$C_8$ alkynyl; $C_1$–$C_8$ haloalkyl; $C_3$–$C_8$ haloalkenyl; $C_3$–$C_8$ alkoxyalkyl other than propoxymethyl; $C_2$–$C_8$ alkylthioalkyl; $C_4$–$C_8$ cycloalkylalkyl; $C_5$–$C_8$ cyanoalkyl; $C_4$–$C_8$ alkenyloxyalkyl; phenyl optionally substituted with $R^{13}$; or $C_3$–$C_5$ alkyl substituted with phenyl optionally substituted with $R^{13}$ and $R^{15}$; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

Preferred 3. The compounds of Formula III as defined above wherein:

Q is O;

$R^3$ is halogen; $C_1$–$C_8$ alkyl; $C_2$–$C_8$ alkynyl; $C_3$–$C_8$ cycloalkyl; $C_1$–$C_8$ haloalkyl; $C_1$–$C_8$ alkoxy; $C_1$–$C_8$ haloalkoxy; $C_1$–$C_8$ alkylthio; $C_1$–$C_8$ alkylsulfonyl; $C_2$–$C_8$ alkoxyalkyl, $C_2$–$C_8$ alkylthioalkyl; $C_4$–$C_8$ cycloalkylalkyl; or $C_5$–$C_8$ trialkylsilylalkynyl;

$R^7$ is $C_3$–$C_8$ alkyl; $C_4$–$C_7$ alkenyl; propynyl; $C_2$–$C_8$ haloalkyl; $C_3$–$C_8$ haloalkenyl; $C_2$–$C_8$ alkoxyalkyl; $C_2$–$C_8$ alkylthioalkyl; $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or phenyl, pyridyl, furanyl, or thienyl each optionally substituted with $R^{14}$ and $R^{15}$;

$R^9$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; $C_2$–$C_8$ alkylthioalkyl; $C_4$–$C_8$ cycloalkylalkyl; $C_4$–$C_8$ cyanoalkyl; $C_4$–$C_8$ alkenyloxyalkyl; —$NR^{12}R^{17}$; or $R^3$ and $R^4$ are both iodine and $R^9$ is phenyl optionally substituted with $R^{14}$ and $R^{15}$; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

Preferred 4. The compounds of Preferreds 1, 2, and 3 wherein:

$R^1$ is $C_3$–$C_8$ alkyl; $C_4$–$C_8$ alkenyl; $C_4$–$C_8$ alkynyl; $C_3$–$C_8$ haloalkyl; $C_3$–$C_8$ haloalkenyl; $C_3$–$C_8$ alkoxyalkyl; or thienyl optionally substituted with at least one of $R^{14}$ and $R^{15}$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^{13}$;

$R^3$ is halogen; $C_1$–$C_4$ alkyl; $C_1$–$C_4$ haloalkyl; $C_1$–$C_4$ alkoxy; $C_1$–$C_4$ haloalkoxy; acetylenyl; or trimethylsilylacetylenyl;

$R^5$ is $C_3$–$C_5$ alkyl; $C_4$–$C_7$ alkenyl; $C_3$–$C_5$ alkynyl; $C_3$–$C_8$ haloalkyl; $C_5$–$C_8$ haloalkenyl; $C_3$–$C_8$ alkoxyalkyl; or phenyl or thienyl each optionally substituted with $R^{14}$ and $R^{15}$;

$R^6$ is $C_3$–$C_8$ alkyl; $C_3$–$C_7$ alkenyl; $C_3$–$C_8$ alkynyl; $C_3$–$C_8$ haloalkyl; $C_3$–$C_8$ halo lkenyl; $C_3$–$C_8$ alkoxyalkyl; or phenyl optionally substituted with $R^{13}$;

$R^7$ is $C_3$–$C_8$ alkyl; $C_4$–$C_7$ alkenyl; propynyl; $C_3$–$C_8$ haloalkyl; $C_3$–$C_8$ haloalkenyl; $C_3$–$C_8$ alkoxy; $C_3$–$C_8$ alkoxyalkyl; or phenyl or thienyl each optionally substituted with $R^{14}$ and $R^{15}$;

$R^9$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; —$NR^{12}R^{17}$; or $R^3$ and $R^4$ are both iodine and $R^9$ is phenyl optionally substituted with $R^{14}$ and $R^{15}$; and $R^{14}$ is methyl; ethyl; methoxy; methylthio; halogen; trifluoromethyl; or $N(C_1$–$C_2$ alkyl$)_2$.

Preferred 5. The compounds of Preferred 4 wherein:

$R^1$ is $C_3$–$C_8$ alkyl; $C_4$–$C_8$ alkenyl; $C_4$–$C_8$ alkynyl; $C_3$–$C_8$ haloalkyl, or $C_3$–$C_8$ haloalkenyl;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; or phenyl optionally substituted with $R^{13}$;

$R^3$ is halogen;

$R^4$ is hydrogen or halogen.

$R^5$ is $C_3$–$C_5$ alkyl; $C_4$–$C_7$ alkenyl; $C_3$–$C_5$ alkynyl; $C_3$–$C_8$ haloalkyl; or $C_5$–$C_8$ haloalkenyl; or phenyl optionally substituted with $R^{14}$ and $R^{15}$;

$R^6$ is $C_3$–$C_8$ alkyl; $C_3$–$C_7$ alkenyl; $C_3$–$C_8$ alkynyl; $C_3$–$C_8$ haloalkyl; $C_3$–$C_8$ haloalkenyl; or phenyl optionally substituted with $R^{13}$;

$R^7$ is $C_3$–$C_8$ alkyl; $C_4$–$C_7$ alkenyl; propynyl; $C_3$–$C_8$ haloalkyl; or $C_3$–$C_8$ haloalkenyl; or phenyl optionally substituted with $R^{14}$ and $R^{15}$; and $R^9$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; —$NR^{12}R^{17}$; or $R^3$ and $R^4$ are both iodine and $R^9$ is phenyl optionally substituted with $R^{14}$ and $R^{15}$.

Preferred 6. The compounds of Preferred 5 wherein said compounds are selected from the group:

6-bromo-3-propyl-2-propyloxy-4(3H)-quinazolinone;
6,8-diiodo-3-propyl-2-propyloxy-4(3H)-quinazolinone;
6-iodo-3-propyl-2-propyloxy-4(3H)-quinazolinone; and
6,8-diiodo-3-propyl-2-(phenylamino)-4(3H)-quinazolinone.

It is recognized that some reagents and reaction conditions described below for preparing compounds of Formulae I, II, and III may not be compatible with some functionalities claimed for $R^1$–$R^{17}$, n, m, and Q. In these cases, the incorporation of protection/deprotection sequences into the synthesis may be necessary in order to obtain the desired products. The cases in which protecting groups are necessary, and which protecting group to use, will be apparent to one skilled in chemical synthesis. See Greene, T. W. and Wuts, P. G. M.; *Protective Groups in Organic Synthesis*, 2nd Ed.; John Wiley & Sons, Inc.; New York, (1980) for suitable protecting groups.

In the following description of the preparation of compounds of Formulae I, II, and III, compounds of Formulae Ia and Ib, IIa–IIc, and IIIa–IIIe are various subsets of the compounds of Formulae I, II, and III. All substituents in compounds of Formulae Ia and Ib, IIa–IIc, and IIIa–IIIe and 2–7 are as defined above for Formulae I, II, and III.

Compounds of this invention can exist as one or more stereoisomers. The various stereoisomers include enantiomers, diastereomers and geometric isomers. One skilled in the art will appreciate that one stereoisomer may be more active than the others and how to separate said stereoisomers. Accordingly, the present invention comprises mixtures, individual stereoisomers, and optically active mixtures of compounds of Formulae I, II, and III as well as agriculturally suitable salts thereof.

The compounds of Formulae I, II, and III can be prepared as described below in Schemes 1–9 and Examples 1–3.

Synthesis of Compounds of Formula I

Compounds of Formula Ia, compounds of Formula I wherein Q is O, can be made by the method illustrated in Scheme 1.

An anthranilic acid (2-aminobenzoic acid) of Formula 2 is condensed with an isothiocyanate of Formula $R^1$—NCS to form the 2-thioquinazolinedione of Formula 3. This condensation is preferably performed in the presence of a base such as triethylamine. S-Methylation of this compound affords the 2-methylthio-4(3H)-quinazolinone of Formula 4.

For the introduction of the $R^2O$ group, the 2-methylthio-4(3H)-quinazolinone of Formula 4 is treated with a mixture of a base, for example sodium hydride, in $R^2OH$ solvent. The reaction mixture is stirred at a temperature from about 0° C. to 120° C. for 1–120 hours. The desired 2-$R^2O$-4(3H)-quinazolinone can be isolated from the reaction mixture by extraction into a water-immiscible solvent, and purified by chromatography or recrystallization. Similar synthetic procedures are described in U.S. Pat. No. 3,755,582, incorporated herein by reference.

Scheme 1

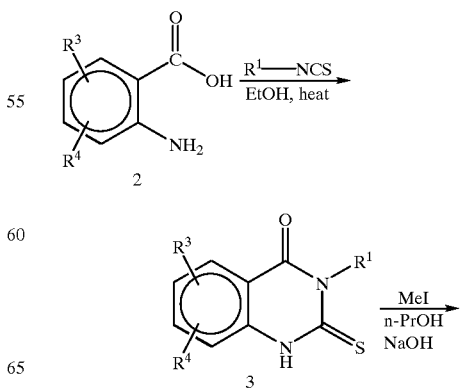

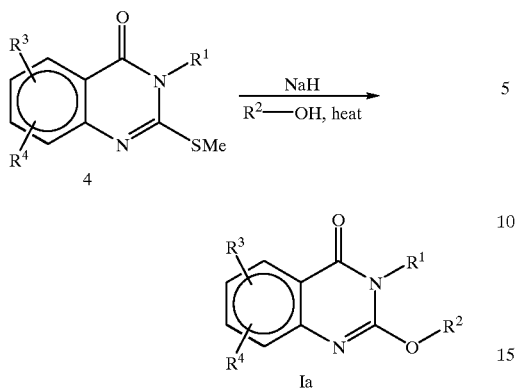

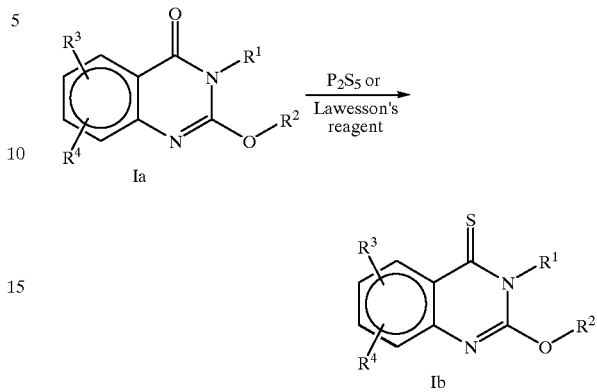

Anthranilic acids of Formula 2 are known or can be prepared by known methods. For example see, March, J. *Advanced Organic Chemistry;* 3rd ed., John Wiley: New York, (1985), p 983. The isothiocyanates of Formula $R^1$—NCS can be prepared from the corresponding amine by treatment with thiophosgene as known in the art. For example, see *J. Heterocycl. Chem.,* (1990), 27, 407.

Alternatively, 2-thioquinazolinediones of Formula 3 can be prepared by treatment of the ($C_1$–$C_4$ alkyl) anthranilic acid ester of Formula 5 with thiophosgene to form the isothiocyanate ester, followed by treatment with an amine of formula $R^1NH_2$ (Scheme 2).

Scheme 2

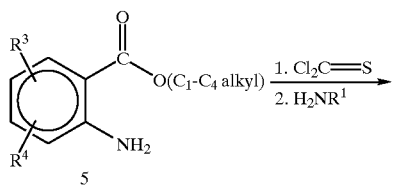

The anthranilic acid ester of Formula 5 is treated with thiophosgene at a temperature from about –20° C. to 100° C. for 1 to 48 hours optionally in an inert solvent. Often this reaction is performed in a biphasic mixture in the presence of a base, such as calcium carbonate, and an acid, such as aqueous hydrochloric acid. The resulting isothiocyanate may be isolated by extraction into a water-immiscible solvent, such as methylene chloride, followed by drying of the organic extracts and evaporation under reduced pressure. Alternatively, the isothiocyanate can be combined in situ with the amine of Formula $H_2NR^1$ and stirred at about –20° C. to 50° C. for 0.1 to 24 hours. The desired 2-thioquinazolinediones of Formula 3 can be isolated from the reaction mixture by aqueous extraction, and purified by chromatography or recrystallization. Similar synthetic procedures are described in *J. Heterocycl. Chem.,* (1990), 27, 407.

Compounds of Formula Ib, compounds of Formula I wherein Q is S, can be prepared as illustrated in Scheme 3.

Treatment of the quinazolinone of Formula Ia with phosphorous pentasulfide or Lawesson's reagent [2,4-bis(4-methoxyphenyl)-1,3-dithia-2,4-diphosphetane-2,4-disulfide] in an inert solvent such as dioxane at a temperature from 0° C. to the reflux temperature of the solvent for 0.1 to 72 hours affords the quinazolinethione of Formula Ib. This procedure is described in the literature, for example see U.S. Pat. No. 3,755,582.

Synthesis of Compounds of Formula II

4(3H)-Quinazolinones of Formula IIa, compounds of Formula II wherein n is 0 and Q is O, can be prepared by a modification of the synthesis illustrated in Scheme 1. As illustrated in Scheme 4, the 2-thioquinazolinedione of Formula 6 is alkylated with $R^6$-X wherein X is a typical leaving group such as Br, I, $CH_3SO_3$ (OMs), or (4-$CH_3$—Ph)$SO_3$ (OTs) to afford the 2-$R^6$S-4(3H)-quinazolinone of Formula IIa. One or more equivalents of a base can be used to accelerate the process. Bases such as sodium hydroxide and sodium hydride are suitable.

Scheme 4

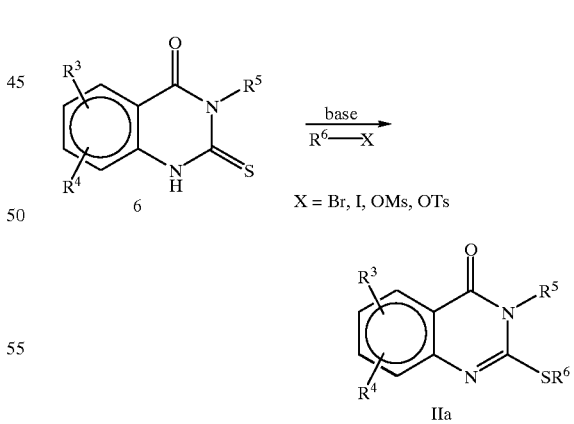

Typically, the 2-thioquinazolinedione is dissolved or dispersed in an inert solvent such as dimethylformamide and treated with a base at a temperature from about –20° C. to 60° C. with a base. The reaction mixture may then be heated to just above ambient temperature to the reflux temperature of the solvent for 0.1 to 24 hours to effect deprotonation. After cooling, the reaction mixture is cooled and treated with $R^6$-X and stirred for 0.1–24 hours at a temperature from about 20° C. to the reflux temperature of the solvent. The quinazolinone of Formula IIa can be isolated by extraction into a water-immiscible solvent, and purified by chromatography or recrystallization.

2-Thioquinazolinediones of Formula 6 are prepared as described above in Schemes 1 and 2 for 2-thioquinazolinediones of Formula 3.

4(3H)-Quinazolinones of Formula IIb, compounds of Formula II wherein Q is O and n is 1 or 2, can be prepared by oxidation of the corresponding —$SR^6$ compound of Formula Ia using well-known procedures for oxidation of sulfur (Scheme 5). For example, see March, J. *Advanced Organic Chemistry;* 3rd ed., John Wiley: New York, (1985), p 1089.

Scheme 5

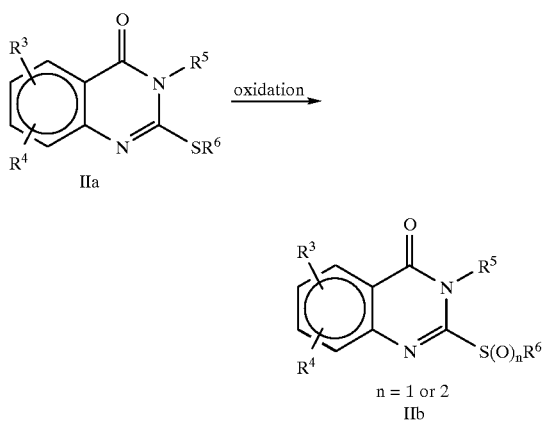

4(3H)-Quinazolinethiones of Formula IIc, compounds of Formula II wherein Q is S, can be prepared by treatment of the corresponding quinazolinone with phosphorous pentasulfide or Lawesson's reagent as described in U.S. Pat. No. 3,755,582 and above for compounds of Formula Ib (Scheme 6).

Scheme 6

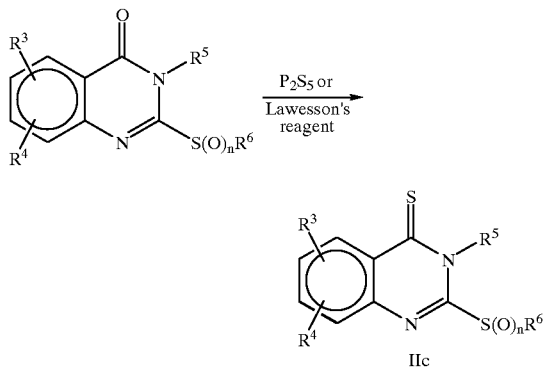

Synthesis of Compounds of Formula III

4(3H)-Quinazolinones of Formula IIIa, compounds of Formula III wherein Q is O, can be prepared by the method illustrated in Scheme 7. This method is described in detail in U.S. Pat. No. 3,867,384 and incorporated herein by reference.

Scheme 7

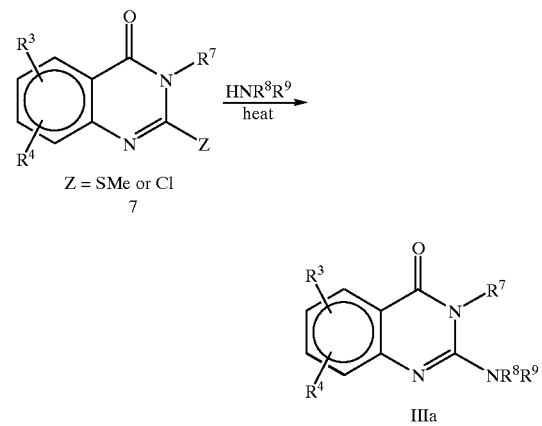

One method of preparation of compounds of Formula IIIa is by treatment of a 2-methylthio-4(3H)-quinazolinone of Formula 7 (Z=SMe) with an excess of an amine of Formula $HNR^8R^9$ at about 150° C. to 175° C. A second method is to contact a 2-chloro-4(3H)-quinazolinone of Formula 7 (Z=Cl) with one equivalent of $HNR^8R^9$ and one equivalent of an acid scavenger, for example triethylamine, or with two equivalents of $HNR^8R^9$, at a temperature between 60° C. and 120° C. optionally in the presence of a solvent.

The preparation of compounds of Formula 7 wherein Z is SMe is described above and in U.S. Pat. No. 3,755,582. The synthesis of compounds of Formula 7 wherein Z is Cl is described in U.S. Pat. No. 3,867,384. Amines of Formula $HNR^8R^9$ are commercially available or can be prepared by well-known methods (March, J. *Advanced Organic Chemistry;* 3rd ed., John Wiley: New York, (1985), p 1153).

In addition to the methods described above, compounds of Formula Ia and IIa can be prepared by displacement of the 2-chlorine in the appropriate 4(3H)-quinazolinone, rather than by displacement of the 2-$SCH_3$ group (Scheme 1) or S-alkylation of the thiocarbonyl (Scheme 4).

As described above for compounds of Formula Ib and IIc, quinazolinethiones of Formula IIIb can be prepared by treatment of the corresponding quinazolinone with $P_2S_5$ or Lawesson's reagent (Scheme 8).

Scheme 8

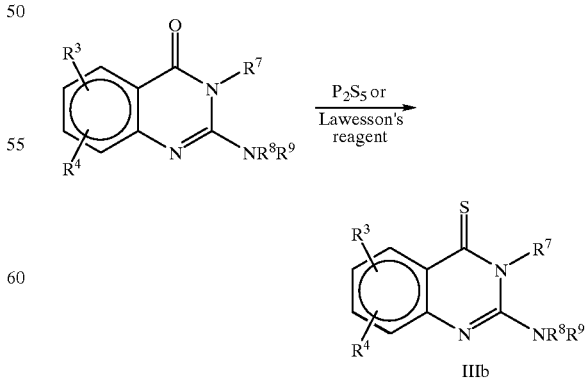

Alternatively, 4(3H)-quinazolinones and quinazolinethiones of Formulae IIId and IIIe, compounds of Formula III wherein $R^8$=—C(=O)$R^{12}$, can be prepared by acylation of the corresponding quinazolinones or quinazolinethione wherein $R^8$=H (Formula IIIc) as illustrated in Scheme 9.

Scheme 9

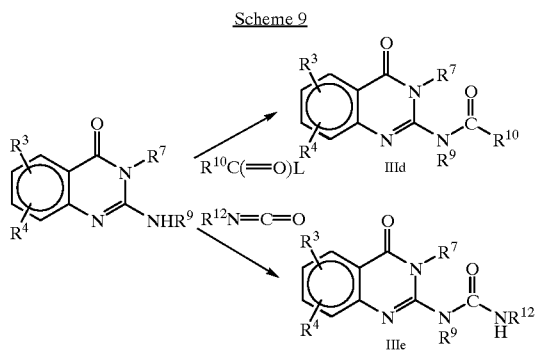

The quinazolinones of Formula IIIc can be treated with an acylating agent of Formula $R^{10}$C(=O)L wherein L is an appropriate leaving group such as chlorine or OC(=O)(H or $C_1$–$C_4$ alkyl). In a similar fashion, compounds of Formula III wherein $R^8$ is –C(=O)NH$R^{12}$ (Formula IIIe) can be prepared by condensing quinazolinones of Formula IIIc with isocyanates of Formula $R^{14}$N=C=O using well known procedures.

Salts of compounds of Formulae I, II, and III can be formed by treating the free base of the corresponding compound with strong acids such as hydrochloric or sulfuric acid. Salts can also be prepared by alkylation of a tertiary amine group in the molecule to form, for example, the trialkylammonium salt. N-Oxides of compounds of Formulae I, II, and III can be made by oxidizing the corresponding reduced nitrogen compound with a strong oxidizing agent such as meta-chloroperoxybenzoic acid.

EXAMPLE 1

Synthesis of 6-Bromo-3-propyl-2-propyloxy-4(3H)-quinazolinone

All reactions were conducted under a nitrogen atmosphere.

Step A

To a solution of 200 mL of ethanol containing 37 g of 2-amino-5-bromobenzoic acid was added dropwise 17.72 mL of n-propyl isothiocyanate with stirring. The mixture was heated at reflux for 8 h, allowed to cool to room temperature and stirred for approximately 60 h. The mixture was then cooled to approximately 5° C. and filtered to obtain 15.42 g of an off-white solid.

Step B

To a solution containing 15.4 g of the product of Step A dissolved in 100 mL of 10% propanolic sodium hydroxide was added 3.2 mL of iodomethane with stirring. The mixture was stirred at room temperature for 10 min, then heated at reflux for 1.5 h, and then allowed to cool to room temperature and stirred overnight. The reaction mixture was filtered to obtain 11.47 g of a white solid. The white solid was purified by column chromatography on silica gel eluting with hexane and then 9:1 hexane:ethyl acetate. Collection and evaporation of those fractions containing the least polar component (according to thin layer chromatography, 6:1 hexane/ethyl acetate mixture as the development solvent) yielded 6.55 g of a white solid, m.p. 97–99° C.

Step C

To 150 mL of propanol cooled to approximately –60° C. was added 0.83 g of 1 NaH (60% active in oil) with stirring.

To this mixture at –60° C. was added 6.5 g of the purified product obtained in Step B. The mixture was allowed to warm to room temperature and stirred for approximately 48 h to yield a clear solution. The reaction solution was poured into water and extracted twice with diethyl ether. The ether extracts were washed twice with water, dried over magnesium sulfate, filtered and the filtrate was then evaporated to yield 10.3 g of an oil. Thin layer chromatography indicated starting material and desired product were both present.

Step D

To propanol cooled to –50° C. was added 0.60 g of NaH (60% active in oil) with stirring. To this mixture at –40° C. was added the product of Step C and the mixture was allowed to warm to room temperature and stirred for approximately 72 h. The mixture was then heated at reflux for 30 min, cooled to room temperature, poured into water and extracted twice with diethyl ether. The combined ether extracts were washed three times with water, dried over magnesium sulfate, filtered and the filtrate was evaporated to yield an oil. The oil was purified by column chromatography on silica gel eluting with hexane followed by 9:1 hexane/ethyl acetate. Collection and evaporation of the fractions containing only the least polar component (according to thin layer chromatography on silica gel, 9:1 hexane/ethyl acetate mixture as the development solvent) yielded 4.46 g of the title compound as a white solid, m.p. 57–59° C.: $^1$H NMR (400 MHz, CDCl$_3$) δ 8.3 (s,1H), 7.7 (m,1H), 7.3 (m,1H), 4.43 (t,2H), 4.05 (t,2H), 1.85 (m,2H), 1.7 (m,2H), 1.06 (t,3H), 0.97 (t,3H).

EXAMPLE 2

Synthesis of 6-Bromo-3-n-butyl-2-n-propylamino-4 (3H)-quinazolinone

Step A

To a solution of 200 mL of ethanol containing 15.15 g of 2-amino5-bromobenzoic acid was added dropwise 9.3 mL of n-butyl isothiocyanate with stirring. To this reaction solution was added 9.77 mL of triethylamine. The reaction solution was heated at reflux for 4 h during which time a solid precipitated. The reaction mixture was cooled to 0° C. and filtered to obtain 19.89 g of an off-white solid, m.p. 246–248° C.

Step B

To a solution containing 7 g of the product of Step A suspended in 50 mL of chloroform was added 1.97 mL of sulfinyl chloride with stirring. The solution was heated at reflux for 5 h, then cooled to room temperature. The reaction solution was poured into water and extracted twice with methylene chloride. The organic extracts were dried over magnesium sulfate, filtered and the filtrate was then evaporated to a yellow solid. The solid was purified by column chromatography on silica gel eluting with 6:1 hexane/ethyl acetate. Collection and evaporation of the fractions containing only the second-least polar component (according to thin layer chromatography on silica gel, 4:1 hexane/ethyl acetate mixture as the development solvent) yielded 3.2 g of white solid. m.p. 56–58° C.

Step C

To a solution containing 1.02 g of the purified product obtained in Step B dissolved in 25 mL of tetrahydrofuran was added 0.5 mL of n-propylamine. The reaction mixture was stirred for approximately 24 h at room temperature. The reaction was then filtered and the filtrate was evaporated to obtain an oil. The oil was dissolved in diethyl ether and washed twice with water and once with brine. The ether solution was dried over magnesium sulfate, filtered and the filtrate was then evaporated to yield 0.74 g of the title compound as a white solid. m.p. 71–73° C.: $^1$H NMR (400 MHz, CDCl$_3$) 0.97–1.04 (m,6H), 1.45 (m,2H), 1.70 (m,4H), 3.50 (m,2H), 4.00 (t,2H), 4.50 (s,1H), 7.24 (d,1H), 7.60 (d,1H), 8.20 (s,1H).

EXAMPLE 3

Synthesis of 6-Bromo-3-n-propyl-2-n-propylthio-4 (3H)-quinazolinone

Step A

To a solution of 150 mL isopropanol containing 29.7 g of 2-amino-5-bromobenzoic acid was added dropwise 15.64 mL of n-propyl isothiocyanate with stirring. The reaction mixture was then heated at reflux for 15 h. The reaction mixture was cooled to 0° C. and filtered to obtain 9.12 g of an off-white solid.

Step B

To a solution containing 0.34 g of the product of Step A suspended in 20 mL of 10% propanolic sodium hydroxide was added 0.22 mL of iodopropane with stirring. The reaction mixture was stirred 1.5 h at room temperature. The reaction was poured into water and extracted twice with methylene chloride. The methylene chloride extractions were washed twice with water, dried over magnesium sulfate, filtered, and the filtrate was then evaporated to yield a white solid. The solid was purified by column chromatography on silica gel eluting with 8:1 hexane/ethyl acetate. Collections and evaporation of the fractions containing only the least-polar component (according to thin layer chromatography on silica gel, 6:1 hexane/ethyl acetate mixture as the development solvent) yielded 0.27 g of the title compound as a white solid, m.p. 65–67° C.: $^1$H NMR (400 MHz, CDCl$_3$): δ 0.99–1.10 (m,6H), 1.80 (m,4H), 3.25 (t,2H), 4.10 (t,2H), 7.41 (d,1H), 7.78 (d,1H), 8.30 (s,1H).

Using the procedures outlined in Schemes 1–9 and Examples 1–3, the compounds of Tables 1–12 hereinafter can be prepared. The compounds referred to in the Tables which follow are illustrated below:

The following abbreviations are used in the Tables which follow. All alkyl groups are the normal isomers unless indicated otherwise. See structures in Index Tables A–C hereinafter for ring system numbering.

| | |
|---|---|
| t = tertiary | MeO = methoxy |
| s = secondary | Pr = propyl |
| n = normal | CN = cyano |
| i = iso | c = cyclo |
| Me = methyl | MeS = methylthio |
| Et = ethyl | Bu = butyl |
| Ph = phenyl | |

TABLE 1

Compounds of Formula I wherein: Q = O, R$^2$ = n-Pr, R$^3$ = 6-Br, R$^4$ = H, and

| R$^1$ | R$^1$ | R$^1$ | R$^1$ |
|---|---|---|---|
| n-Pr | n-Bu | n-pentyl | n-hexyl |
| n-decyl | i-Pr | i-Bu | s-Bu |
| c-propyl | c-butyl | c-pentyl | 2-butenyl |
| 3-butenyl | 2-butynyl | 3-butynyl | CF$_3$ |
| 2-Cl—Et | 3-Br—Pr | CH$_2$CH=CHCl | CH$_2$C=CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$S(O)CH$_3$ | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$OCH$_2$CH≡CH | (c-hexyl)OCH$_2$ | (c-pentyl)SCH$_2$ |
| CH$_2$CH$_2$SCH$_2$CH=CH$_2$ | CH$_2$CH$_2$SCH$_2$CH≡CH | CH$_2$OCF$_3$ | CH$_2$OCH$_2$CH$_2$Cl |
| CH$_2$OCH$_2$CH=CHCl | CH$_2$OCH$_2$C≡CBr | CH$_2$CH=CHCH$_2$OCH$_3$ | CH$_2$C≡CCH$_2$OCH$_3$ |
| CH$_2$CH=CHCH$_2$SCH$_3$ | CH$_2$C≡CCH$_2$SCH$_3$ | CH$_2$CH$_2$Si(CH$_3$)$_3$ | CH$_2$CH$_2$N(CH$_3$)$_2$ |
| CH$_2$CH$_2$CH$_2$NHCH$_3$ | CH$_2$CH$_2$NO$_2$ | CH$_2$CH$_2$CH$_2$CN | PhCH$_2$ |
| OCH$_2$CH$_2$CH$_3$ | OCH$_2$CH$_2$CF$_3$ | SCH$_2$CH$_3$ | SCCl$_3$ |
| SCH$_2$CH$_2$Cl | NHCH$_2$CH$_2$CH$_3$ | N(CH$_3$)CH$_2$CH$_3$ | Ph |
| 2-pyridinyl | 2-furanyl | 2-thienyl | 2-naphthyl |
| 5-benzofuranyl | 3-benzothienyl | 3-quinolinyl | (4-F-Ph)CH$_2$ |

Compounds of Formula I wherein: Q = O, R$^2$ = n-Pr, R$^3$ = 6-I, R$^4$ = H, and

| R$^1$ | R$^1$ | R$^1$ | R$^1$ |
|---|---|---|---|
| n-Pr | n-Bu | n-pentyl | n-hexyl |
| n-decyl | i-Pr | i-Bu | s-Bu |
| c-propyl | c-butyl | c-pentyl | 2-butenyl |
| 3-butenyl | 2-butynyl | 3-butynyl | CF$_3$ |
| 2-Cl—Et | 3-Br—Pr | CH$_2$CH=CHCl | CH$_2$C=CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$S(O)CH$_3$ | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$OCH$_2$C≡CH | (c-hexyl)OCH$_2$ | (c-pentyl)SCH$_2$ |
| CH$_2$CH$_2$SCH$_2$CH=CH$_2$ | CH$_2$CH$_2$SCH$_2$C≡CH | CH$_2$OCF$_3$ | CH$_2$OCH$_2$CH$_2$Cl |
| CH$_2$OCH$_2$CH=CHCl | CH$_2$OCH$_2$C≡CBr | CH$_2$CH=CHCH$_2$OCH$_3$ | CH$_2$C≡CCH$_2$OCH$_3$ |
| CH$_2$CH=CHCH$_2$SCH$_3$ | CH$_2$C≡CCH$_2$SCH$_3$ | CH$_2$CH$_2$Si(CH$_3$)$_3$ | CH$_2$CH$_2$N(CH$_3$)$_2$ |
| CH$_2$CH$_2$CH$_2$NHCH$_3$ | CH$_2$CH$_2$NO$_2$ | CH$_2$CH$_2$CH$_2$CN | PhCH$_2$ |
| OCH$_2$CH$_2$CH$_3$ | OCH$_2$CH$_2$CF$_3$ | SCH$_2$CH$_3$ | SCCl$_3$ |
| SCH$_2$CH$_2$Cl | NHCH$_2$CH$_2$CH$_3$ | N(CH$_3$)CH$_2$CH$_3$ | PhCH$_2$ |
| 2-pyridinyl | 2-furanyl | 2-thienyl | 2-naphthyl |
| 5-benzofuranyl | 3-benzothienyl | 3-quinolinyl | (2-Me-Ph)CH$_2$CH$_2$ |

TABLE 1-continued

Compounds of Formula I wherein: Q = O, $R^2$ = n-Pr, $R^3$ = 6-I, $R^4$ = 8-I, and

| $R^1$ | $R^1$ | $R^1$ | $R^1$ |
|---|---|---|---|
| n-Pr | n-Bu | n-pentyl | n-hexyl |
| n-decyl | i-Pr | i-Bu | s-Bu |
| c-propyl | c-butyl | c-pentyl | 2-butenyl |
| 3-butenyl | 2-butynyl | 3-butynyl | $CF_3$ |
| 2-Cl—Et | 3-Br—Pr | $CH_2CH$=$CHCl$ | $CH_2C$≡$CCl$ |
| $CH_2OCH_3$ | $CH_2OCH_2CH_3$ | $CH_2SCH_3$ | $CH_2SCH_2CH_3$ |
| $CH_2CH_2SCH_3$ | $CH_2CH_2S(O)CH_3$ | $CH_2CH_2CH_2S(O)_2CH_3$ | (c-pentyl)$CH_2$ |
| $CH_2CH_2OCH_2CH$=$CH_2$ | $CH_2CH_2OCH_2C$≡$CH$ | (c-hexyl)$OCH_2$ | (c-pentyl)$SCH_2$ |
| $CH_2CH_2SCH_2CH$=$CH_2$ | $CH_2CH_2SCH_2C$≡$CH$ | $CH_2OCF_3$ | $CH_2OCH_2CH_2Cl$ |
| $CH_2OCH_2CH$=$CHCl$ | $CH_2OCH_2C$≡$CBr$ | $CH_2CH$=$CHCH_2OCH_3$ | $CH_2C$≡$CCH_2OCH_3$ |
| $CH_2CH$=$CHCH_2SCH_3$ | $CH_2C$≡$CCH_2SCH_3$ | $CH_2CH_2Si(CH_3)_3$ | $CH_2CH_2N(CH_3)_2$ |
| $CH_2CH_2CH_2NHCH_3$ | $CH_2CH_2NO_2$ | $CH_2CH_2CH_2CN$ | $PhCH_2$ |
| $OCH_2CH_2CH_3$ | $OCH_2CH_2CF_3$ | $SCH_2CH_3$ | $SCCl_3$ |
| $SCH_2CH_2Cl$ | $NHCH_2CH_3$ | $N(CH_3)CH_2CH_3$ | (2-Me-Ph)$CH_2CH_2$ |
| 2-pyridinyl | 2-furanyl | 2-thienyl | 2-naphthyl |
| 5-benzofuranyl | 3-benzothienyl | 3-quinolinyl | (4-F-Ph)$CH_2$ |

TABLE 2

Compounds of Formula I wherein: Q = O, $R^1$ = n-Pr, $R^3$ = 6-Br, $R^4$ = H, and

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | allyl | 2-butenyl |
| 3-butenyl | 5-decenyl | propargyl | 2-butynyl |
| 3-butynyl | $CF_3$ | $CH_2CF_3$ | $CH_2CH$=$CHCl$ |
| $CH_2C$≡$CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C$≡$CH$ | $CH_2CH_2SCH_2CH$=$CH_2$ | (c-propyl)$OCH_2$ |
| (c-hexyl)$SCH_2$ | $CH_2CH_2OCF_3$ | $CH_2CH_2SCH_2C$≡$CH$ | $CH_2CH_2CH_2CN$ |
| $CH_2CH_2Si(CH_3)_3$ | —NHPh | $CH_2CH_2OCH_2CCl$=$CH_2$ | $CH_2OCH_2CH_2Cl$ |
| $CH_2(4$-$F$-$Ph)$ | —N($CH_3$)Ph | $CH_2CH_2CH_2N(CH_3)_2$ | $CH_2CH_2CH_2Ph$ |
| $CH_2CH_2CH_2F$ | $CH_2Ph$ | $CH_2CH_2OCH_2CH$=$CH_2$ | $CH_2CH_2Ph$ |
| $CH_2CH_2CH_2NHCH_3$ | $CH_2CH_2NO_2$ | —N=CHPh | $CH_2CH_2(4$-$F$-$Ph)$ |
| —N=$CHCH_2CH_2CH_3$ | —N=$C(CH_3)_2$ | $NHCH_2CH_3$ | $N(CH_3)_2$ |

Compounds of Formula I wherein: Q = O, $R^1$ 3' n-Pr, $R^3$ = 6-I, $R^4$ = H, and

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | allyl | 2-butenyl |
| 3-butenyl | 5-decenyl | propargyl | 2-butynyl |
| 3-butynyl | $CF_3$ | $CH_2CF_3$ | $CH_2CH$=$CHCl$ |
| $CH_2C$≡$CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C$≡$CH$ | $CH_2CH_2SCH_2CH$=$CH_2$ | (c-propyl)$OCH_2$ |
| (c-hexyl)$SCH_2$ | $CH_2CH_2OCF_3$ | $CH_2CH_2SCH_2C$≡$CH$ | $CH_2CH_2CH_2CN$ |
| $CH_2CH_2Si(CH_3)_3$ | $CH_2CH_2CO_2Et$ | $CH_2CH_2OCH_2CCl$=$CH_2$ | $CH_2OCH_2CH_2Cl$ |
| Ph | 4-Me-Ph | $CH_2CH_2CH_2N(CH_3)_2$ | 2-F-Ph |
| 4-MeO-Ph | $CH_2Ph$ | $CH_2CH_2OCH_2CH$=$CH_2$ | $CH_2CH_2Ph$ |
| $CH_2CH_2CH_2NHCH_3$ | $CH_2CH_2NO_2$ | —N=CHPh | $CH_2CH_2(4$-$F$-$Ph)$ |
| —N=$CHCH_2CH_2CH_3$ | —N=$C(CH_3)_2$ | $NHCH_2CH_3$ | $N(CH_3)_2$ |
| 2,4-diCl-Ph | 2,4,6-triF-Ph | 4-$CF_3$-Ph | 2-CN-Ph |
| $CH_2(4$-$F$-$Ph)$ | —NHPh | —N($CH_3$)Ph | $CH_2CH_2CH_2Ph$ |

Compounds of Formula I wherein: Q = O, $R^1$ 3' n-Pr, $R^3$ = 6-I, $R^4$ = 8-I, and

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | allyl | 2-butenyl |
| 3-butenyl | 5-decenyl | propargyl | 2-butynyl |
| 3-butynyl | $CF_3$ | $CH_2CF_3$ | $CH_2CH$=$CHCl$ |
| $CH_2C$≡$CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C$≡$CH$ | $CH_2CH_2SCH_2CH$=$CH_2$ | (c-propyl)$OCH_2$ |
| (c-hexyl)$SCH_2$ | $CH_2CH_2OCF_3$ | $CH_2CH_2SCH_2C$≡$CH$ | $CH_2CH_2CH_2CN$ |

TABLE 2-continued

| | | | |
|---|---|---|---|
| $CH_2CH_2Si(CH_3)_3$ | $CH_2CH_2CO_2Et$ | $CH_2CH_2OCH_2CCl=CH_2$ | $CH_2OCH_2CH_2Cl$ |
| Ph | 4-Me-Ph | $CH_2CH_2CH_2N(CH_3)_2$ | 2-F-Ph |
| 4-MeO-Ph | $CH_2Ph$ | $CH_2CH_2OCH_2CH=CH_2$ | $CH_2CH_2Ph$ |
| $CH_2CH_2CH_2NHCH_3$ | $CH_2CH_2NO_2$ | —N=CHPh | $CH_2CH_2(4\text{-F-Ph})$ |
| —N=CHCH_2CH_2CH_3 | —N=C(CH_3)_2 | $NHCH_2CH_2CH_3$ | $N(CH_3)_2$ |
| 2,4-diCl-Ph | 2,4,6-triF-Ph | 4-$CF_3$-Ph | 2-CN-Ph |
| $CH_2(4\text{-F-Ph})$ | —NHPh | —N($CH_3$)Ph | $CH_2CH_2CH_2Ph$ |

TABLE 3

Compounds of Formula I wherein Q = O and $R^1 = R^2$ = n-Pr, and

| $R^3$ | $R^4$ | $R^3$ | $R^4$ | $R^3$ | $R^4$ |
|---|---|---|---|---|---|
| 6-Cl | H | 6-Me | H | 6-Me$_3$Si | 8-Br |
| 6-Br | 8-Me | 6-Et | 8-Br | 6-Me$_2$N | H |
| 6-I | 8-Br | 6-MeO | H | 6-EtNH | H |
| 6-Cl | 8-Cl | 6-MeS | 8-MeO | 6-Br | 8-Me |
| 6-Br | 8-Cl | 6-SCH$_2$CH=CH$_2$ | H | 6-Br | 8-Et |
| 6-I | 8-I | 6-S(O)$_2$Me | H | 6-i-Pr | H |
| 6-C≡CH | H | 6-Br | 8-CF$_3$ | 6-Br | 8-OCF$_3$ |
| 6-C≡CH | 8-Br | 6-CH$_2$C≡CH | H | 6-CF$_3$O | H |
| 6-c-propyl | H | 6-Br | 7-Br | 6-CH=CH$_2$ | H |
| 6-CF$_3$ | H | 6-OCH$_2$CH=CH$_2$ | H | 6-Br | 7-Me |
| 6-CH$_2$Br | H | 6-Br | 5-Me | 6-Br | 5-Br |
| 6-CH=CHBr | H | 6-(c-propyl)CH$_2$ | H | 8-Br | H |
| 6-CH$_3$OCH$_2$ | H | 6-I | 8-Me | 6-Me | 8-Br |

TABLE 4

Compounds of Formula I wherein Q = S and

| $R^1$ | $R^2$ | $R^3$ | $R^4$ | $R^1$ | $R^2$ | $R^3$ | $R^4$ |
|---|---|---|---|---|---|---|---|
| n-Pr | n-Pr | 6-Br | H | nb-Pr | n-Pr | 6-Br | 8-Me |
| n-Pr | n-Pr | 6-I | 8-I | n-Pr | n-Pr | 6-C≡CH | H |
| n-Pr | n-Pr | 6-I | H | n-Pr | allyl | 6-I | H |
| n-Pr | n-Pr | 6-I | 8-I | n-Pr | butyl | 6-Br | H |
| 3-butenyl | n-Pr | 6-Br | H | n-Pr | butyl | 6-I | H |
| n-Pr | allyl | 6-Br | H | n-Pr | allyl | 6-Br | H |
| n-Pr | butyl | 6-I | H | n-Pr | butyl | 6-Br | H |
| 2-Br-Et | n-Pr | 6-I | 8-I | n-butyl | n-Pr | 6-I | 8-I |
| PhCH$_2$ | n-Pr | 6-Br | H | 2-thienyl | allyl | 6-I | H |
| 2-thienyl | allyl | 6-Br | H | 2-thienyl | allyl | 6-I | H |
| n-Pr | PhCH$_2$ | 6-I | 8-I | n-Pr | PhCH$_2$ | 6-I | H |
| n-Pr | PhCH$_2$CH$_2$ | 6-Br | H | n-Pr | pentyl | 6-Br | H |

TABLE 5

Compounds of Formula II wherein: Q = O, n is 0, $R^6$ = n-Pr, $R^3$ = 6-Br, $R^4$ = H, and

| $R^5$ | $R^5$ | $R^5$ | $R^5$ |
|---|---|---|---|
| n-Pr | n-Bu | n-pentyl | n-octyl |
| n-decyl | i-Pr | i-Bu | s-Bu |
| CH$_2$CH$_2$OCH$_3$ | propargyl | 4-pentynyl | 2-butenyl |
| 3-butenyl | 2-butynyl | 3-butynyl | CF$_3$ |
| 2-Cl-Et | 3-Br-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$S(O)CH$_3$ | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$OCH$_2$C≡CH | (c-hexyl)OCH$_2$ | (c-pentyl)SCH$_2$ |
| CH$_2$CH$_2$SCH$_2$CH=CH$_2$ | CH$_2$CH$_2$SCH$_2$CH≡CH | CH$_2$OCF$_3$ | CH$_2$OCH$_2$CH$_2$Cl |
| CH$_2$OCH$_2$CH=CHCl | CH$_2$OCH$_2$C≡CBr | CH$_2$CH=CHCH$_2$OCH$_3$ | CH$_2$C≡CCH$_2$OCH$_3$ |
| CH$_2$CH=CHCH$_2$SCH$_3$ | CH$_2$C≡CCH$_2$SCH$_3$ | CH$_2$CH$_2$Si(CH$_3$)$_3$ | CH$_2$CH$_2$N(CH$_3$)$_2$ |
| CH$_2$CH$_2$CH$_2$NHCH$_3$ | CH$_2$CH$_2$NO$_2$ | CH$_2$CH$_2$CH$_2$CN | SCCl$_3$ |
| OCH$_2$CH$_2$CH$_3$ | OCH$_2$CH$_2$CF$_3$ | SCH$_2$CH$_3$ | Ph |
| SCH$_2$CH$_2$Cl | NHCH$_2$CH$_2$CH$_3$ | N(CH$_3$)CH$_2$CH$_3$ | 2-naphthyl |
| 4-MeS-Ph | 2-furanyl | 2-thienyl | 4-F-Ph |
| 5-benzofuranyl | 3-benzothienyl | 2-F-4-Cl-Ph | 3-CF$_3$O-Ph |
| 2-F-4-Me-Ph | 3-MeO-Ph | 4-Ph-Ph | CH$_2$Ph |
| | | | 4-PhO-Ph |

TABLE 5-continued

Compounds of Formula II wherein: Q = O, n is 0, $R^6$ = n-Pr, $R^3$ = 6-I, $R^4$ = H, and

| $R^5$ | $R^5$ | $R^5$ | $R^5$ |
| --- | --- | --- | --- |
| n-Pr | n-Bu | n-pentyl | n-octyl |
| n-decyl | i-Pr | i-Bu | s-Bu |
| $CH_2CH_2OCH_3$ | propargyl | 4-pentynyl | 2-butenyl |
| 3-butenyl | 2-butynyl | 3-butynyl | $CF_3$ |
| 2-Cl-Et | 3-Br-Pr | $CH_2CH=CHCl$ | $CH_2C\equiv CCl$ |
| $CH_2OCH_3$ | $CH_2OCH_2CH_3$ | $CH_2SCH_3$ | $CH_2SCH_2CH_3$ |
| $CH_2CH_2SCH_3$ | $CH_2CH_2S(O)CH_3$ | $CH_2CH_2CH_2S(O)_2CH_3$ | (c-pentyl)$CH_2$ |
| $CH_2CH_2OCH_2CH=CH_2$ | $CH_2CH_2OCH_2C\equiv CH$ | (c-hexyl)$OCH_2$ | (c-pentyl)$SCH_2$ |
| $CH_2CH_2SCH_2CH=CH_2$ | $CH_2CH_2SCH_2C\equiv CH$ | $CH_2OCF_3$ | $CH_2OCH_2CH_2Cl$ |
| $CH_2OCH_2CH=CHCl$ | $CH_2OCH_2C\equiv CBr$ | $CH_2CH=CHCH_2OCH_3$ | $CH_2C\equiv CCH_2OCH_3$ |
| $CH_2CH=CHCH_2SCH_3$ | $CH_2C\equiv CCH_2SCH_3$ | $CH_2CH_2Si(CH_3)_3$ | $CH_2CH_2N(CH_3)_2$ |
| $CH_2CH_2CH_2NHCH_3$ | $CH_2CH_2NO_2$ | $CH_2CH_2CH_2CN$ | $CH_2Ph$ |
| $OCH_2CH_2CH_3$ | $OCH_2CH_2CF_3$ | $SCH_2CH_3$ | $SCCl_3$ |
| $SCH_2CH_2Cl$ | $NHCH_2CH_2CH_3$ | $N(CH_3)CH_2CH_3$ | Ph |
| 4-MeS-Ph | 2-furanyl | 2-thienyl | 2-naphthyl |
| 5-benzofuranyl | 3-benzothienyl | 4-Ph-Ph | 4-F-Ph |
| 2-F-4-Me-Ph | 3-MeO-Ph | 2-F-4-Cl-Ph | 3-$CF_3$O-Ph |
|  |  |  | 4-PhO-Ph |

TABLE 6

Compounds of Formula II wherein: Q = O, n = 0, $R^5$ = n-Pr, $R^3$ = 6-Br, $R^4$ = H, and

| $R^6$ | $R^6$ | $R^6$ | $R^6$ |
| --- | --- | --- | --- |
| $CH_2C(CH_3)=CH_2$ | t-Bu | i-Pr | n-Bu |
| i-Bu | s-Bu | n-pentyl | n-hexyl |
| n-decyl | $CH_2CH(CH_3)CH_2CH_3$ | allyl | 2-butenyl |
| 3-butenyl | 5-heptenyl | propargyl | 2-butynyl |
| 3-butynyl | $CF_3$ | $CH_2CF_3$ | $CH_2CH=CHCl$ |
| $CH_2C\equiv CBr$ | $CH_2CH_2O(CH_2)_2CH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C\equiv CH$ | $CH_2CH_2SCH_2CH=CH_2$ | (c-proyl)$OCH_2$ |
| (c-hexyl)$SCH_2$ | $CH_2CH_2OCF_3$ | $CH_2CH_2SCH_2C\equiv CH$ | $(CH_2)_4CN$ |
| $CH_2CH_2Si(CH_3)_3$ | $CH_2CH_2CH_2CO_2Et$ | $CH_2CH_2OCH_2CCl=CH_2$ | $CH_2OCH_2CH_2Cl$ |
| Ph | 4-Me-Ph | $CH_2CH_2CH_2N(CH_3)_2$ | 2-F-Ph |
| 4-MeO-Ph | $(CH_2)_4Ph$ | $CH_2CH_2OCH_2CH=CH_2$ | $CH_2CH_2CH_2Ph$ |
| $CH_2CH_2CH_2NHCH_3$ | $CH_2CH_2NO_2$ | —N=CHPh | $CH_2CH_2(4\text{-F-Ph})$ |
| 4-Cl-Ph | 2-Me-Ph | $NHCH_2CH_2CH_3$ | $N(CH_3)_2$ |
| 2,4-diCl-Ph | 2,4,6-triF-Ph | 4-$CF_3$-Ph | 2-CN-Ph |
|  | —NHPh | —N($CH_3$)Ph | $CH_2CH_2CH_2(4\text{-F-Ph})$ |

Compounds of Formula II wherein: Q = O, n = 0, $R^5$ = n-Pr, $R^3$ = 6-I, $R^4$ = H, and

| $R^6$ | $R^6$ | $R^6$ | $R^6$ |
| --- | --- | --- | --- |
| $CH_2C(CH_3)=CH_2$ | t-Bu | i-Pr | n-Bu |
| i-Bu | s-Bu | n-pentyl | n-hexyl |
| n-decyl | $CH_2CH(CH_3)CH_2CH_3$ | allyl | 2-butenyl |
| 3-butenyl | 5-heptenyl | propargyl | 2-butynyl |
| 3-butynyl | $CF_3$ | $CH_2CF_3$ | $CH_2CH=CHCl$ |
| $CH_2C\equiv CBr$ | $CH_2CH_2O(CH_2)_2CH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C\equiv CH$ | $CH_2CH_2SCH_2CH=CH_2$ | (c-proyl)$OCH_2$ |
| (c-hexyl)$SCH_2$ | $CH_2CH_2OCF_3$ | $CH_2CH_2SCH_2C\equiv CH$ | $(CH_2)_4CN$ |
| $CH_2CH_2Si(CH_3)_3$ | $CH_2CH_2CH_2CO_2Et$ | $CH_2CH_2OCH_2CCl=CH_2$ | $CH_2OCH_2CH_2Cl$ |
| Ph | 4-Me-Ph | $CH_2CH_2CH_2N(CH_3)_2$ | 2-F-Ph |
| 4-MeO-Ph | $CH_2Ph$ | $CH_2CH_2OCH_2CH=CH_2$ | $CH_2CH_2CH_2Ph$ |
| $CH_2CH_2CH_2NHCH_3$ | $CH_2CH_2NO_2$ | —N=CHPh | $CH_2CH_2(4\text{-F-Ph})$ |
| 4-Cl-Ph | 2-Me-Ph | $NHCH_2CH_2CH_3$ | $N(CH_3)_2$ |
| 2,4-diCl-Ph | 2,4,6-triF-Ph | 4-$CF_3$-Ph | 2-CN-Ph |
|  | —NHPh | —N($CH_3$)Ph |  |

TABLE 7

Compounds of Formula I wherein Q = O and $R^5 = R^6$ = n-Pr, and

| $R^3$ | $R^4$ | $R^3$ | $R^4$ | $R^3$ | $R^4$ |
|---|---|---|---|---|---|
| 6-Cl | H | 6-Me | H | 6-Me$_3$Si | 8-Br |
| 6-Br | 8-Me | 6-Et | 8-Br | 6-Me$_2$N | H |
| 6-I | 8-Br | 6-MeO | H | 6-EtNH | H |
| 6-Cl | 8-Cl | 6-MeS | 8-MeO | 6-Br | 8-Me |
| 6-Br | 8-Cl | 6-SCH$_2$CH=CH$_2$ | H | 6-Br | 8-Et |
| 6-I | 8-I | 6-S(O)$_2$Me | H | 6-i-Pr | H |
| 6-C≡CH | H | 6-Br | 8-CF$_3$ | 6-Br | 8-OCF$_3$ |
| 6-C≡CH | 8-Br | 6-CH$_2$C≡CH | H | 6-CF$_3$O | H |
| 6-c-propyl | H | 6-Br | 7-Br | 6-CH=CH$_2$ | H |
| 6-CF$_3$ | H | 6-OCH$_2$CH=CH$_2$ | H | 6-Br | 7-Me |
| 6-CH$_2$Br | H | 6-Br | 5-Me | 6-Br | 5-Br |
| 6-CH=CHBr | H | 6-(c-propyl)CH$_2$ | H | 8-Br | H |
| 6-MeOCH$_2$ | H | 6-I | 8-Me | 6-Me | 8-Br |

TABLE 8

| $R^5$ | $R^6$ | $R^3$ | $R^4$ |
|---|---|---|---|
| Compounds of Formula II wherein Q = O, n = 1 | | | |
| n-Pr | n-Pr | 6-Br | H |
| n-Pr | n-Pr | 6-I | 8-I |
| n-Pr | n-Pr | 6-I | H |
| n-Pr | n-Pr | 6-I | 8-I |
| 3-butenyl | n-Pr | 6-Br | H |
| n-Pr | allyl | 6-Br | H |
| n-Pr | butyl | 6-I | H |
| 2-Br-Et | n-Pr | 6-I | 8-I |
| Ph | n-Pr | 6-Br | H |
| 4-F-Ph | n-Pr | 6-I | H |
| 2-thienyl | butyl | 6-Br | H |
| n-Pr | PhCH$_2$CH$_2$CH$_2$ | 6-Br | H |

TABLE 8-continued

| $R^5$ | $R^6$ | $R^3$ | $R^4$ |
|---|---|---|---|
| Compounds of Formula II wherein Q = O, n = 2 | | | |
| n-Pr | n-Pr | 6-Br | H |
| n-Pr | n-Pr | 6-I | 8-I |
| n-Pr | n-Pr | 6-I | H |
| n-Pr | n-Pr | 6-I | 8-I |
| 3-butenyl | n-Pr | 6-Br | H |
| n-Pr | allyl | 6-Br | H |
| n-Pr | butyl | 6-I | H |
| 2-Br-Et | n-Pr | 6-I | 8-I |
| Ph | n-Pr | 6-Br | H |
| 4-F-Ph | n-Pr | 6-I | H |
| 2-thienyl | butyl | 6-Br | H |
| n-Pr | pentyl | 6-Br | H |

TABLE 9

Compounds of Formula III wherein: Q = O, $R^8$ = H, $R^9$ = n-Pr, $R^3$ = 6-Br, $R^4$ = H, and

| $R^7$ | $R^7$ | $R^7$ | $R^7$ |
|---|---|---|---|
| n-Pr | n-Bu | n-pentyl | n-hexyl |
| c-hexyl | i-Pr | i-Bu | s-Bu |
| c-propyl | c-butyl | c-pentyl | 2-butenyl |
| 3-butenyl | 2-propynyl | 3-pentynyl | CH$_2$CF$_3$ |
| 2-Cl-Et | 3-Br-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$S(O)CH$_3$ | CH$_2$CH$_2$CH$_2$S(O)$_2$CH$_3$ | n-decyl |
| CH$_2$CH$_2$OCH$_2$CH=CH$_2$ | CH$_2$CH$_2$OCH$_2$C≡CH | (c-hexyl)OCH$_2$ | (c-pentyl)SCH$_2$ |
| CH$_2$CH$_2$SCH$_2$CH=CH$_2$ | CH$_2$CH$_2$SCH$_2$C≡CH | CH$_2$OCF$_3$ | CH$_2$OCH$_2$CH$_2$Cl |
| CH$_2$OCH$_2$CH=CHCl | CH$_2$OCH$_2$C≡CBr | CH$_2$CH=CHCH$_2$OCH$_3$ | CH$_2$C≡CCH$_2$OCH$_3$ |
| CH$_2$CH=CHCH$_2$SCH$_3$ | CH$_2$C≡CCH$_2$SCH$_3$ | CH$_2$CH$_2$Si(CH$_3$)$_3$ | CH$_2$CH$_2$N(CH$_3$)$_2$ |
| CH$_2$CH$_2$CH$_2$NHCH$_3$ | CH$_2$CH$_2$NO$_2$ | CH$_2$CH$_2$CH$_2$CN | SCCl$_3$ |
| OCH$_2$CH$_2$CH$_3$ | OCH$_2$CH$_2$CF$_3$ | SCH$_2$CH$_3$ | Ph |
| SCH$_2$CH$_2$Cl | NHCH$_2$CH$_2$CH$_3$ | N(CH$_3$)CH$_2$CH$_3$ | 2-naphthyl |
| 2-pyridinyl | 2-furanyl | 2-thienyl | 4-F-Ph |
| 5-benzofuranyl | 3-benzothienyl | 3-quinolinyl | 3-CF$_3$O-Ph |
| 2-F-4-Me-Ph | 3-MeO-Ph | 2-F-4-Cl-Ph | 4-Cl-Ph |
| 4-MeS-Ph | 4-PhO-Ph | 4-Ph-Ph | |

TABLE 9-continued

| Compounds of Formula III wherein: Q = O, $R^8$ = H, $R^9$ = n-Pr, $R^3$ = 6-I, $R^4$ = H, and | | | |
|---|---|---|---|
| $R^7$ | $R^7$ | $R^7$ | $R^7$ |
| n-Pr | n-Bu | n-pentyl | n-hexyl |
| c-hexyl | i-Pr | i-Bu | s-Bu |
| c-propyl | c-butyl | c-pentyl | 2-butenyl |
| 3-butenyl | 2-propynyl | 3-pentynyl | $CH_2CF_3$ |
| 2-Cl-Et | 3-Br-Pr | $CH_2CH\!=\!CHCl$ | $CH_2C\!\equiv\!CCl$ |
| $CH_2OCH_3$ | $CH_2OCH_2CH_3$ | $CH_2SCH_3$ | $CH_2SCH_2CH_3$ |
| $CH_2CH_2SCH_3$ | $CH_2CH_2S(O)CH_3$ | $CH_2CH_2CH_2S(O)_2CH_3$ | n-decyl |
| $CH_2CH_2OCH_2CH\!=\!CH_2$ | $CH_2CH_2OCH_2C\!\equiv\!CH$ | (c-hexyl)$OCH_2$ | (c-propyl)$CH_2$ |
| $CH_2CH_2SCH_2CH\!=\!CH_2$ | $CH_2CH_2SCH_2C\!\equiv\!CH$ | $CH_2OCF_3$ | $CH_2OCH_2CH_2Cl$ |
| $CH_2OCH_2CH\!=\!CHCl$ | $CH_2OCH_2C\!\equiv\!CBr$ | $CH_2CH\!=\!CHCH_2OCH_3$ | $CH_2C\!\equiv\!CCH_2OCH_3$ |
| $CH_2CH\!=\!CHCH_2SCH_3$ | $CH_2C\!\equiv\!CCH_2SCH_3$ | $CH_2CH_2Si(CH_3)_3$ | $CH_2CH_2N(CH_3)_2$ |
| $CH_2CH_2CH_2NHCH_3$ | $CH_2CH_2NO_2$ | $CH_2CH_2CH_2CN$ | $SCCl_3$ |
| $OCH_2CH_2CH_3$ | $OCH_2CH_2CF_3$ | $SCH_2CH_3$ | Ph |
| $SCH_2CH_2Cl$ | $NHCH_2CH_2CH_3$ | $N(CH_3)CH_2CH_3$ | 2-naphthyl |
| 2-pyridinyl | 2-furanyl | 2-thienyl | 4-F-Ph |
| 5-benzoifuranyl | 3-benzothienyl | 3-quinolinyl | 3-$CF_3$O-Ph |
| 2-F-4-Me-Ph | 3-MeO-Ph | 2-F-4-Cl-Ph | 4-Cl-Ph |
| 4-MeS-Ph | 4-PhO-Ph | 4-Ph-Ph | |

| Compounds of Formula III wherein: Q = O, $R^8$ = H, $R^9$ = n-Pr, $R^3$ = 6-I, $R^4$ = 8-I, and | | | |
|---|---|---|---|
| $R^7$ | $R^7$ | $R^7$ | $R^7$ |
| n-Pr | n-Bu | n-pentyl | n-hexyl |
| c-hexyl | i-Pr | i-Bu | s-Bu |
| c-propyl | c-butyl | c-pentyl | 2-butenyl |
| 3-butenyl | 2-propynyl | 3-pentynyl | $CH_2CF_3$ |
| 2-Cl-Et | 3-Br-Pr | $CH_2CH\!=\!CHCl$ | $CH_2C\!\equiv\!CCl$ |
| $CH_2OCH_3$ | $CH_2OCH_2CH_3$ | $CH_2SCH_3$ | $CH_2SCH_2CH_3$ |
| $CH_2CH_2SCH_3$ | $CH_2CH_2S(O)CH_3$ | $CH_2CH_2CH_2S(O)_2CH_3$ | n-decyl |
| $CH_2CH_2OCH_2CH\!=\!CH_2$ | $CH_2CH_2OCH_2C\!\equiv\!CH$ | (c-hexyl)$OCH_2$ | (c-propyl)$CH_2$ |
| $CH_2CH_2SCH_2CH\!=\!CH_2$ | $CH_2CH_2SCH_2C\!\equiv\!CH$ | $CH_2OCF_3$ | $CH_2OCH_2CH_2Cl$ |
| $CH_2OCH_2CH\!=\!CHCl$ | $CH_2OCH_2C\!\equiv\!CBr$ | $CH_2CH\!=\!CHCH_2OCH_3$ | $CH_2C\!\equiv\!CCH_2OCH_3$ |
| $CH_2CH\!=\!CHCH_2SCH_3$ | $CH_2C\!\equiv\!CCH_2SCH_3$ | $CH_2CH_2Si(CH_3)_3$ | $CH_2CH_2N(CH_3)_2$ |
| $CH_2CH_2CH_2NHCH_3$ | $CH_2CH_2NO_2$ | $CH_2CH_2CH_2CN$ | $NHCH_3$ |
| $OCH_2CH_2CH_3$ | $OCH_2CH_2CF_3$ | $SCH_2CH_3$ | $SCCl_3$ |
| $SCH_2CH_2Cl$ | $NHCH_2CH_2CH_3$ | $N(CH_3)CH_2CH_3$ | Ph |
| 2-pyridinyl | 2-furanyl | 2-thienyl | 2-naphthyl |
| 5-benzoifuranyl | 3-benzothienyl | 3-quinolinyl | 4-F-Ph |
| 2-F-4-Me-Ph | 3-MeO-Ph | 2-F-4-Cl-Ph | 3-$CF_3$O-Ph |
| 4-MeS-Ph | 4-PhO-Ph | 4-Ph-Ph | 4-Cl-Ph |

TABLE 10

| Compounds of Formula III wherein: Q = O, $R^7$ = n-Pr, $R^8$ = H, $R^3$ = 6-Br, $R^4$ = H, and | | | |
|---|---|---|---|
| $R^9$ | $R^9$ | $R^9$ | $R^9$ |
| Et | t-Bu | i-Pr | n-Bu |
| i-Bu | s-Bu | n-pentyl | n-hexyl |
| n-decyl | $CH_2CH(CH_3)CH_2CH_3$ | allyl | 2-butenyl |
| 3-butenyl | 5-heptenyl | propargyl | 2-butynyl |
| 3-butynyl | $CH_2CH_2CH_2Cl$ | $CH_2CH_2CF_3$ | $CH_2CH\!=\!CHCl$ |
| $CH_2C\!\equiv\!CBr$ | $(CH_2)_2OCH_2CH_3$ | $CH_2OCH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C\!\equiv\!CH$ | $CH_2CH_2SCH_2CH\!=\!CH_2$ | (c-propyl)$OCH_2$ |
| (c-hexyl)$SCH_2$ | $CH_2CH_2OCF_3$ | $CH_2CH_2SCH_2C\!\equiv\!CH$ | $(CH_2)_3CN$ |
| $CH_2CH_2Si(CH_3)_3$ | $CH_2CH_2CO_2Et$ | $CH_2OCH_2CCl_2\!=\!CH_2$ | $CH_2CH_2CH_2Cl$ |
| —N=CHPh | —NHPh | $CH_2CH_2CH_2N(CH_3)_2$ | c-propyl |
| c-hexyl | —NC(=O)NHPh | $CH_2CH_2OCH_2CH\!=\!CH_2$ | —NC(=S)NHPh |
| $CH_2CH_2CH_2NHCH_3$ | $CH_2CH_2NO_2$ | —$NHCH_2CH_2CH_3$ | $N(CH_3)_3^+I^-$ |
| —N=CHCH$_2$CH$_2$CH$_3$ | —N=C(CH$_3$)$_2$ | $NHCH_2CH_2CH_3$ | $N(CH_3)_2$ |
| —$OCH_2CH_2CH_3$ | $(CH_2)_3$(2,4,6-triF-Ph) | $CH_2$(4-$CF_3$-Ph) | —$OCH_2CH(CH_3)_2$ |

| Compounds of Formula III wherein: Q = O, $R^7$ = n-Pr, $R^8$ = H, $R^3$ = 6-I, $R^4$ = H, and | | | |
|---|---|---|---|
| $R^9$ | $R^9$ | $R^9$ | $R^9$ |
| Et | t-Bu | i-Pr | n-Bu |
| i-Bu | s-Bu | n-pentyl | n-hexyl |
| n-decyl | $CH_2CH(CH_3)CH_2CH_3$ | allyl | 2-butenyl |
| 3-butenyl | 5-heptenyl | propargyl | 2-butynyl |

TABLE 10-continued

| | | | |
|---|---|---|---|
| 3-butynyl | $CH_2CH_2CH_2Cl$ | $CH_2CH_2CF_3$ | $CH_2CH=CHCl$ |
| $CH_2C\equiv CBr$ | $(CH_2)_2OCH_2CH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C\equiv CH$ | $CH_2CH_2SCH_2CH=CH_2$ | (c-propyl)$OCH_2$ |
| (c-hexyl)$SCH_2$ | $CH_2CH_2OCF_3$ | $CH_2CH_2SCH_2C\equiv CH$ | $(CH_2)_3CN$ |
| $CH_2CH_2Si(CH_3)_3$ | $CH_2CH_2CO_2Et$ | $CH_2CH_2OCH_2CCl=CH_2$ | $CH_2OCH_2CH_2Cl$ |
| —N=CHPh | —NHPh | $CH_2CH_2CH_2N(CH_3)_2$ | c-propyl |
| c-hexyl | —NC(=O)NHPh | $CH_2CH_2OCH_2CH=CH_2$ | —NC(=S)NHPh |
| $CH_2CH_2CH_2NHCH_3$ | $CH_2CH_2NO_2$ | —NHCH$_2$CH$_2$CH$_3$ | $N(CH_3)_3{}^+I^-$ |
| —N=CHCH$_2$CH$_2$CH$_3$ | —N=C(CH$_3$)$_2$ | NHCH$_2$CH$_2$CH$_3$ | $N(CH_3)_2$ |
| —OCH$_2$CH$_2$CH$_3$ | $(CH_2)_3$(2,4,6-triF-Ph) | $CH_2$(4-CF$_3$-Ph) | —OCH$_2$CH(CH$_3$)$_2$ |

Compounds of Formula III wherein: Q = O, $R^7$ = n-Pr, $R^8$ = H, $R^3$ = 6-I, $R^4$ = 8-I, and

| $R^9$ | $R^9$ | $R^9$ | $R^9$ |
|---|---|---|---|
| Et | t-Bu | i-Pr | n-Bu |
| i-Bu | s-Bu | n-pentyl | n-hexyl |
| n-decyl | $CH_2CH(CH_3)CH_2CH_3$ | allyl | 2-butenyl |
| 3-butenyl | 5-heptenyl | propargyl | 2-butynyl |
| 3-butynyl | $CH_2CH_2CH_2Cl$ | $CH_2CH_2CF_3$ | $CH_2CH=CHCl$ |
| $CH_2C\equiv CBr$ | $(CH_2)_2OCH_2CH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl-Et | $CH_2CH_2OCH_2C\equiv CH$ | $CH_2CH_2SCH_2CH=CH_2$ | (c-propyl)$OCH_2$ |
| (c-hexyl)$SCH_2$ | $CH_2CH_2OCF_3$ | $CH_2CH_2SCH_2C\equiv CH$ | $(CH_2)_3CN$ |
| $CH_2CH_2Si(CH_3)_3$ | $CH_2CH_2CO_2Et$ | $CH_2CH_2OCH_2CCl=CH_2$ | $CH_2OCH_2CH_2Cl$ |
| —N=CHPh | —NHPh | $CH_2CH_2CH_2N(CH_3)_2$ | c-propyl |
| c-hexyl | —NC(=O)NHPh | $CH_2CH_2OCH_2CH=CH_2$ | —NC(=S)NHPh |
| $CH_2CH_2CH_2NHCH_3$ | $CH_2CH_2NO_2$ | —NHCH$_2$CH$_2$CH$_3$ | $N(CH_3)_3{}^+I^-$ |
| —N=CHCH$_2$CH$_2$CH$_3$ | —N=C(CH$_3$)$_2$ | NHCH$_2$CH$_2$CH$_3$ | $N(CH_3)_2$ |
| —OCH$_2$CH$_2$CH$_3$ | $(CH_2)_3$(2,4,6-triF-Ph) | $CH_2$(4-CF$_3$-Ph) | —OCH$_2$CH(CH$_3$)$_2$ |
| Ph | 4-F-Ph | 2-Me-Ph | 2,4-DiCl-Ph |

TABLE 11

Compounds of Formula III wherein Q = O and $R^8$ = H, $R^7$ = $R^9$ = n-Pr, and

| $R^3$ | $R^4$ | $R^3$ | $R^4$ | $R^3$ | $R^4$ |
|---|---|---|---|---|---|
| 6-Cl | H | 6-Me | H | 6-Me$_3$Si | H |
| 6-Br | 8-Me | 6-Et | 8-Br | 6-Me$_2$N | H |
| 6-I | 8-Br | 6-MeO | H | 6-EtNH | H |
| 6-Cl | 8-Cl | 6-MeS | 8-MeO | 6-Br | 8-Me |
| 6-Br | 8-Cl | 6-SCH$_2$CH=CH$_2$ | H | 6-Br | 8-Et |
| 6-I | 8-I | 6-S(O)$_2$Me | H | 6-i-Pr | H |
| 6-C≡CH | H | 6-Br | 8-CF$_3$ | 6-Br | 8-OCF$_3$ |
| 6-C≡CH | 8-Br | 6-CH$_2$C≡CH | H | 6-CF$_3$O | H |
| 6-c-propyl | H | 6-Br | 7-Br | 6-CH=CH$_2$ | H |
| 6-CF$_3$ | H | 6-OCH$_2$CH=CH$_2$ | H | 6-Br | 7-Me |
| 6-CH$_2$Br | H | 6-Br | 5-Me | 6-Br | 5-Br |
| 6-CH=CHBr | H | 6-(c-propyl)CH$_2$ | H | 8-Br | H |
| 6-CH$_3$OCH$_2$ | H | 6-I | 8-Me | 6-Me | 8-Br |

| $R^7$ | $R^9$ | $R^3$ | $R^4$ | $R^7$ | $R^9$ | $R^3$ | $R^4$ |
|---|---|---|---|---|---|---|---|
| Compounds of Formula III wherein Q = S, $R^8$ = H | | | | Compounds of Formula III wherein Q = O, $R^8$ = C(=O)OCH$_3$ | | | |
| n-Pr | n-Pr | 6-Br | H | n-Pr | n-Pr | 6-Br | H |
| n-Pr | n-Pr | 6-I | 8-I | n-Pr | n-Pr | 6-I | 8-I |
| n-Pr | n-Pr | 6-I | H | n-Pr | n-Pr | 6-I | H |
| n-Pr | n-Pr | 6-I | 8-I | n-Pr | n-Pr | 6-I | 8-I |
| 3-butenyl | n-Pr | 6-Br | H | 3-butenyl | n-Pr | 6-Br | H |
| n-Pr | allyl | 6-Br | H | n-Pr | allyl | 6-Br | H |
| n-Pr | Et | 6-I | H | n-Pr | Et | 6-I | H |
| 2-Br-Et | n-Pr | 6-I | 8-I | 2-Br-Et | n-Pr | 6-I | 8-I |
| Ph | n-Pr | 6-Br | H | Ph | n-Pr | 6-Br | H |
| 4-F-Ph | n-Pr | 6-I | H | 4-F-Ph | n-Pr | 6-I | H |
| 2-thienyl | Et | 6-Br | H | 2-thienyl | Et | 6-Br | H |
| n-Pr | Ph | 6-I | 8-I | n-Pr | Ph | 6-I | 8-I |
| n-Pr | NH(CH$_2$)$_2$CH$_3$ | 6-Br | H | n-Pr | (CH$_2$)$_3$Cl | 6-Br | H |

-continued

| $R^7$ | $R^9$ | $R^3$ | $R^4$ |
|---|---|---|---|
| Compounds of Formula III wherein Q = O, $R^8$ = Me | | | |
| n-Pr | n-Pr | 6-Br | H |
| n-Pr | n-Pr | 6-I | 8-I |
| n-Pr | n-Pr | 6-I | H |
| n-Pr | n-Pr | 6-I | 8-I |
| 3-butenyl | n-Pr | 6-Br | H |
| n-Pr | allyl | 6-Br | H |
| n-Pr | Et | 6-I | H |
| 2-Br-Et | n-Pr | 6-I | 8-I |
| Ph | n-Pr | 6-Br | H |
| 4-F-Ph | n-Pr | 6-I | H |
| 2-thienyl | Et | 6-Br | H |
| n-Pr | Ph | 6-I | 8-I |
| n-Pr | $(CH_2)_3Cl$ | 6-Br | H |
| Compounds of Formula III wherein Q = O, $R^8$ = C(=O)$CH_3$ | | | |
| n-Pr | n-Pr | 6-Br | H |
| n-Pr | n-Pr | 6-I | 8-I |
| n-Pr | n-Pr | 6-I | H |
| n-Pr | n-Pr | 6-I | 8-I |
| 3-butenyl | n-Pr | 6-Br | H |
| n-Pr | allyl | 6-Br | H |
| n-Pr | Et | 6-I | H |
| 2-Br-Et | n-Pr | 6-I | 8-I |
| Ph | n-Pr | 6-Br | H |
| 4-F-Ph | n-Pr | 6-I | H |
| 2-thienyl | Et | 6-Br | H |
| n-Pr | Ph | 6-I | 8-I |
| n-Pr | $(CH_2)_3Cl$ | 6-Br | H |

Formulation/Utility

Compounds of this invention will generally be used in formulation with an agriculturally suitable composition. The fungicidal compositions of the present invention comprise an effective amount of at least one compound of Formula I, II, or III as defined above and at least one of (a) a surfactant, (b) an organic solvent, and (c) at least one solid or liquid diluent. Useful formulations can be prepared in conventional ways. They include dusts, granules, pellets, solutions, suspensions, emulsions, wettable powders, emulsifiable concentrates, dry flowables and the like. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents and solvents are described in Marsden, *Solvents Guide,* 2nd Ed., Interscience, New York, (1950). *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, (1964), list surfactants and recommended uses. All formulations can contain minor amounts of additives to reduce foam, caking, corrosion, microbiological growth, and the like.

Methods for formulating such compositions are well known. Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations,* Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering,* Dec. 4, 1967, pp 147–148, *Perry's Chemical Engineer's Handbook,* 4th Ed., McGraw-Hill, New York, (1963), pp 8–57 and following, and WO 91/13546. Pellets can be prepared as described in U.S. Pat. No. 4,172,714. Water-dispersible and water-soluble granules can be prepared as taught in DE 3,246,493.

For further information regarding the art of formulation, see U.S. Pat. No. 3,235,361, Col. 6, line 16 through Col. 7, line 19 and Examples 10 through 41; U.S. Pat. No. 3,309, 192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, (1961), pp 81–96; and Hance et al., *Weed Control Handbook,* 8th Ed., Blackwell Scientific Publications, Oxford, (1989).

In the following Examples, all percentages are by weight and all formulations are prepared in conventional ways. Compound 1 refers to the compound described in Index Table A hereinafter.

Example A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 37 | 10.0% |
| attapulgite granules (low volative matter, 0.71/0.30 mm, U.S.S. No. 25–50 sieves) | 90.0%. |

Example C

Extruded Pellet

| | |
|---|---|
| Compound 25 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 37 | 20.0% |
| blend of oil soluble sulfonates and polyoxyethylene ethers | 10.0% |
| isophorone | 70.0%. |

The compounds of this invention are useful as plant disease control agents, especially for the control of cereal powdery mildews (e.g., *Erysiphe graminis f. sp. tritici*, the causal agent of wheat powdery mildew). The present invention therefore further comprises a method for controlling plant diseases caused by fungal plant pathogens comprising applying to the plant or portion thereof to be protected, or to the plant seed or seedling to be protected, an effective amount of a compound of Formula I, II, or III or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Cercosporidium personatum, Cercospora arachidicola. Pseudocercosporella herpotrichoides, Cercospora beticola, Botrytis cinerea, Monilinia fructicola, Pyricularia oryzae, Podosphaera leucotricha, Venturia inaequalis. Erysiphe graminis, Uncinula necatur, Puccinia recondita, Puccinia graminis, Hemileia vastatrix. Puccinia striiformis, Puccinia arachidis, Rhizoctonia solani. Sphaerotheca fuliginea, Fusarium oxysporum, Verticillium dahliae, Pythium aphanidermatum, Phytophthora megasperma* and other generea and species closely related to these pathogens.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as acephate, avermectin B, azinphosmethyl, bifenthrin, biphenate, buprofezin, carbofuran, chlordimeform, chlorpyrifos, cyfluthrin, deltamethrin, diazinon, diflubenzuron, dimethoate, esfenvalerate, fenpropathrin, fenvalerate, fipronil, flucythrinate, flufenprox, fluvalinate, fonophos, isofenphos, malathion, metaldehyde, methamidophos, methidathion, methomyl, methoprene, methoxychlor, monocrotophos, oxamyl, parathion-methyl, permethrin, phorate, phosalone, phosmet, phosphamidon, pirimicarb, profenofos, rotenone, sulprofos, terbufos, tetrachlorvinphos, thiodicarb, tralomethrin, trichlorfon and triflumuron; fungicides such as benomyl, blasticidin S, bromuconazole, captafol, captan, carbendazim, chloroneb, chlorothalonil, copper oxychloride, copper salts, cymoxanil, cyproconazole, cyrodinil, dichloran, diclobutrazol, diclomezine, difenoconazole, diniconazole, dodine, edifenphos, epoxyconazole fenarimol, fenbuconazole, fenpropidine, fenpropimorph, fluquinconazole, flusilazol, flutolanil, flutriafol, folpet, furalaxyl, hexaconazole, ipconazole, iprobenfos, iprodione, isoprothiolane, kasugamycin, mancozeb, maneb, mepronil, metalaxyl, metconazole, myclobutanil, neo-asozin, oxadixyl, penconazole, pencycuron, phosethyl-Al, probenazole, prochloraz, propiconazole, pyrifenox, pyrimethanil, pyroquilon, sulfur, tebuconazole, tetraconazole, thiabendazole, thiophanate-methyl, thiuram, triadimefon, triadimenol, tricyclazole, triticonazole, uniconzole, validamycin and vinclozolin; nematocides such as aldoxycarb, fenamiphos and fosthietan; bactericides such as oxytetracyline, streptomycin and tribasic copper sulfate; acaricides such as amitraz, binapacryl, chlorobenzilate, cyhexatin, dicofol, dienochlor, fenbutatin oxide, hexythiazox, oxythioquinox, propargite and tebufenpyrad; and biological agents such as Bacillus thuringiensis and baculovirus.

In certain instances, combinations with other fungicides having a similiar spectrum of control but a different mode of action will be particularly advantageous for resistance management. Preferred combinations comprise a compound of Formula I, II, or III, and a fungicide selected from the group flusilazole, cyproconazole, tetraconazole, fenpropimorph, fenpropidine, cymoxanil, benomyl, carbendazim, mancozeb, and maneb.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A, B, and C for compound descriptions.

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests.

Test A

The test suspension was sprayed to the point of run-off on wheat seedlings. The following day the seedlings were inoculated with a spore dust of *Erysiphe graminis f. sp. tritici*, (the causal agent of wheat powdery mildew) and incubated in a growth chamber at 20° C. for 7 days, after which disease ratings were made.

Test B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

Test C

The test suspension was sprayed to the point of run-off on tomato seedlings. The following day the seedlings were inoculated with a spore suspens on of *Phytophthora infestans* (the causal agent of potato and tomato late blight) and incubated in a saturated atmosphere at 20° C. for 24 h, and then moved to a growth chamber at 20° C. for 5 days. after which disease ratings were made.

Test D

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h. after which disease ratings were made.

Test E

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

In the Tables below, $^a=^1$H NMR data for oils are listed in Index Table D

Index TABLE A

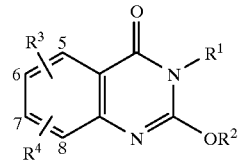

Ia

Compounds of Formula Ia:

| Cmpd No. | $R^1$ | $R^2$ | $R^3$ | $R^4$ | m.p.$^a$(°C.) |
|---|---|---|---|---|---|
| 1 | $CH_2CH_2CH_3$ | $CH_2CH_2CH_3$ | 6-Br | H | 57–59 |
| 2 | $CH_2CH_2CH_3$ | $CH_2CH_2CH_3$ | 7-Cl | H | 57–60 |
| 3 | $CH_2CH_2CH_3$ | $CH_2CH_2CH_3$ | 5-Cl | H | 69–75 |
| 4 | $CH_2CH_2CH_3$ | $CH_2CH_2CH_3$ | 8-Me | H | 47–49 |
| 5 | $CH_2CH_2CH_3$ | $CH_2CH_2CH_3$ | 5-Me | H | oil |
| 6 | $CH_2CH_2CH_3$ | $CH_2CH_2CH_3$ | 6-Me | H | 47–50 |
| 7 | $CH_2CH_2CH_3$ | $CH_2CH_2CH_3$ | 6-OMe | 7-OMe | 112–114 |
| 8 | $CH_2CH_2CH_3$ | $CH_2CH_2CH_3$ | 7-F | H | oil |
| 9 | $CH_2CH_2CH_3$ | $CH_2CH_2CH_3$ | 7-$NO_2$ | H | 64–66 |
| 10 | $CH_2CH_2CH_3$ | $CH_2CH_2CH_3$ | 6-OMe | H | 49–52 |
| 11 | $CH_2CH_2CH_3$ | $CH_2CH_2CH_3$ | 6-Me | 8-Me | 81–84 |
| 12 | $CH_2CH_2CH_3$ | $CH_2CH_2CH_3$ | 6-C≡CH | H | 105–107 |
| 13 | $CH_2CH_2CH_3$ | $CH_2CH_2CH_3$ | 6-F | H | 60–62 |
| 14 | $CH_2CH_2CH_3$ | $CH_2CH_2CH_3$ | 6-Cl | H | 64–66 |
| 15 | $CH_2CH_2CH_3$ | $CH_2CH=CH_2$ | 6-Cl | H | 78–80 |
| 16 | $CH_2CH_2CH_3$ | $CH_2CH=CH_2$ | 6-Br | H | 73–75 |
| 17 | $CH_2CH_2CH_3$ | $CH_2CH_2CH_3$ | 6-Cl | 8-Cl | 78–80 |
| 18 | $CH_2CH_2CH_3$ | $CH_2CH_2CH_3$ | 6-Br | 8-Br | 89–94 |
| 22 | $CH_2CH_2CH_3$ | $(CH_2)_3CH_3$ | 6-Br | H | 58–59 |
| 23 | $CH_2CH_2CH_3$ | i-Pr | 6-Br | H | 45–46 |
| 25 | $CH_2CH_2CH_3$ | $CH_2CH_2CH_3$ | 6-I | H | 48–49 |
| 26 | $CH_2CH_2CH_3$ | $(CH_2)_4CH_3$ | 6-Br | H | 56–57 |
| 27 | $CH_2CH_2CH_3$ | $(CH_2)_5CH_3$ | 6-Br | H | oil |
| 28 | $CH_2CH_2CH_3$ | i-Pr | 6-Cl | H | 48–49 |
| 29 | $(CH_2)_3CH_3$ | $CH_2CH_2CH_3$ | 6-Br | H | 56–58 |
| 30 | $CH_2CH_2CH_3$ | $CH_2CH_2CH=CH_2$ | 6-Cl | H | oil |
| 31 | $CH_2CH_2CH_3$ | $CH_2CH_2C(CH_3)_3$ | 6-Br | H | 70–72 |
| 32 | $CH_2CH_2CH_3$ | $(CH_2)_3CH_2SCH_3$ | 6-Br | H | 86–91 |
| 33 | $CH_2CH_2CH_3$ | $CH_2CH_2CH=CH_2$ | 6-Br | H | oil |
| 34 | $CH_2CH_2CH_3$ | $(CH_2)_4CH_3$ | 6-Cl | H | oil |
| 35 | $CH_2CH_2CH_3$ | $(CH_2)_4CH_3$ | 6-I | H | 47–49 |
| 36 | $CH_2CH_2CH_3$ | $CH_2CH_2CH=CH_2$ | 6-I | H | 43–46 |
| 37 | $CH_2CH_2CH_3$ | $CH_2CH_2CH_3$ | 6-I | 8-I | 135–138 |
| 38 | $(CH_2)_3CH_3$ | $(CH_2)_3CH_3$ | 6-Br | H | oil |
| 39 | $CH_2CH_2CH_3$ | $(CH_2)_2CH_2Ph$ | 6-Br | H | 72–74 |
| 40 | $CH_2CH_2CH_3$ | $CH_2CH_2OCH_3$ | 6-Br | H | 55–57 |
| 41 | $CH_2CH_2CH_3$ | $CH_2CH_2N(CH_3)_2$ | 6-Br | H | 39–42 |
| 42 | $CH_2CH_2CH_3$ | $CH_2CH_2N(CH_3)_2 \cdot HCl$ | 6-Br | H | 215–230 |
| 43 | $(CH_2)_3N(CH_3)_2$ | $CH_2CH_2CH_3$ | 6-Br | H | oil |
| 44 | $(CH_2)_3OCH_3$ | $CH_2CH_2CH_3$ | 6-Br | H | 61–64 |
| 45 | $CH_2CH(CH_3)_2$ | $CH_2CH_2CH_3$ | 6-Br | H. | 50–55 |
| 46 | (c-propyl)$CH_2$ | $CH_2CH_2CH_3$ | 6-Br | H | 99–101 |
| 47 | $CH(CH_3)Et$ | $CH_2CH_2CH_3$ | 6-Br | H | oil |
| 48 | $(CH_2)_4CH_3$ | $(CH_2)_4CH_3$ | 6-Br | H | oil |
| 49 | $CH_2CH_2CH_3$ | $CH_2CH_2CH_3$ | 6-$NO_2$ | H | 68–75 |
| 50 | $CH_2CH_2CH_3$ | $CH_2CH_2CH_3$ | 6-C≡C—$SiMe_3$ | H | 76–78 |
| 51 | $CH_2CH_2CH_3$ | $CH_2CH_2CH_2CH_3$ | 6-I | H | 54–57 |
| 52 | $(CH_2)_3CH_3$ | $(CH_2)_3CH_3$ | 6-I | H | 50–51 |
| 53 | $(CH_2)_3CH_3$ | $CH_2CH_2CH_3$ | 6-I | H | 50–52 |
| 54 | $(CH_2)_3SCH_3$ | $CH_2CH_2CH_3$ | 6-Br | H | 69–71 |
| 55 | $CH_2CH_2CH_3$ | $CH_2CH_2N^+(CH_3)_3I^-$ | 6-Br | H | 223–225 |
| 56 | $(CH_2)_3N^+(CH_3)_3I^-$ | $CH_2CH_2CH_3$ | 6-Br | H | 200–204 |

Index TABLE A-continued

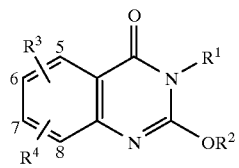

Ia

Compounds of Formula Ia:

| Cmpd No. | R¹ | R² | R³ | R⁴ | m.p.ᵃ(°C.) |
|---|---|---|---|---|---|
| 57 | (CH₂)₃N(CH₃)₂HCl | CH₂CH₂CH₃ | 6-Br | H | 145–150 |
| 58 | CH₂CHBrCH₂Br | CH₂CH₂CH₃ | 6-Br | H | 118–121 |
| 59 | CH₂CH₂(N-1,4-morpholinyl) | CH₂CH₂CH₃ | 6-Br | H | 103–105 |

Index TABLE B

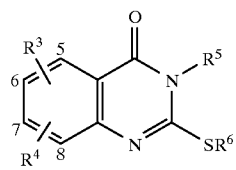

IIa

Compounds of Formula IIa:

| Cmpd No. | R⁵ | R⁶ | R³ | R⁴ | m.p. (°C.) |
|---|---|---|---|---|---|
| 60 | CH₂CH₂CH₃ | CH₂CH₂CH₃ | 6-I | H | 90–92 |
| 61 | CH₂CH₂CH₃ | CH₂CH₂CH₃ | 6-Br | H | 65–67 |

Index TABLE C

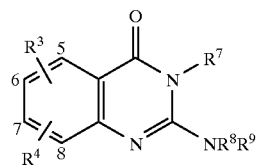

IIIa

Compounds of Formula IIIa:

| Cmpd No. | R⁷ | R⁹ | R⁸ | R³ | R⁴ | m.p.ᵃ (°C.) |
|---|---|---|---|---|---|---|
| 62 | CH₂CH₂CH₃ | CH₂CH₂CH₃ | H | 6-Br | H | 107–111 |
| 63 | CH₂CH₂CH₃ | CH₂CH₂CH₃ | CH₂CH₂CH₃ | 6-Br | H | oil |
| 64 | CH₂CH₂CH₃ | CH₂CH₂CH₃ | H | 6-I | H | 109–111 |
| 65 | CH₂CH₂CH₃ | (CH₂)₃CH₃ | H | 6-Br | H | 87–88 |
| 66 | CH₂CH₂CH₃ | (CH₂)₃CH₃ | H | 6-I | H | 84–85 |
| 67 | CH₂CH₂CH₃ | CH₂CH(CH₃)₂ | H | 6-I | H | 117–119 |
| 68 | CH₂CH₂CH₃ | CH₂CH₂CH₃ | H | 6-I | 8-I | 122–126 |
| 69 | (CH₂)₃CH₃ | CH₂CH₂CH₃ | H | 6-Br | H | 71–73 |
| 70 | (CH₂)₃CH₃ | (CH₂)₃CH₃ | H | 6-Br | H | oil |
| 71 | CH₂CH₂CH₃ | (CH₂)₃CH₃ | H | 6-I | 8-I | 126–131 |
| 72 | (CH₂)₃CH₃ | (CH₂)₃CH₃ | H | 6-I | H | oil |
| 73 | (CH₂)₃CH₃ | CH₂CH₂CH₃ | H | 6-I | H | oil |

Index TABLE C-continued

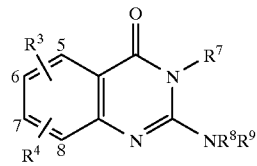

IIIa

Compounds of Formula IIIa:

| Cmpd No. | $R^7$ | $R^9$ | $R^8$ | $R^3$ | $R^4$ | m.p.$^a$ (°C.) |
|---|---|---|---|---|---|---|
| 74 | $(CH_2)_3CH_3$ | $CH_2CH_2CH_3$ | H | 6-I | 8-I | 116–118 |
| 75 | $(CH_2)_3CH_3$ | $(CH_2)_3CH_3$ | H | 6-I | 8-I | 115–116 |
| 76 | $CH_3CH_2CH_3$ | $CH_2CH=CH_2$ | H | 6-F | H | 84–88 |
| 77 | $CH_3CH_2CH_3$ | $CH_2CH=CH_2$ | R | 6-Br | H | 104–106 |
| 79 | $CH_3CH_2CH_3$ | $CH_2CH_2CH=CH_2$ | H | 6-Br | H | 72–75 |
| 80 | $CH_2CH_2CH_3$ | Ph | H | 6-I | 8-I | 159–162 |

INDEX TABLE D

| Cmpd No. | $^1$H NMR Data$^b$ |
|---|---|
| 5 | 7.46(dd, 1H), 7.29(d, 1H), 7.04(d, 1H), 4.42(t, 2H), 4.02(m, 2H), 2.84(s, 3H), 1.85(m, 2H), 1.71(m, 2H), 1.06(t, 3H), 0.98 (t, 3H). |
| 8 | 8.17(dd, 1H), 7.09(dd, 1H), 7.00(dt, 1H), 4.43(t, 2H), 4.05 (m, 2H), 1.73(m, 2H), 1.07(t, 3H), 0.97(t, 3H). |
| 27 | 0.93–0.99(2-t, 6H), 1.37(m, 4H), 1.48(m, 2H), 1.75(m, 2H), 1.80(m, 2H), 4.05(t, 2H), 4.46(t, 2H), 7.34(d, 1H), 7.70(d, 1H), 8.30(s, 1H). |
| 30 | 0.94–0.98(t, 3H), 1.70(m, 2H), 2.59(m, 2H), 4.02(t, 2H), 4.53 (t, 2H), 5.19(dd, 2H), 5.90(m, 1H), 7.40(d, 1H), 7.59(d, 1H), 8.12(s, 1H). |
| 33 | 0.93–0.98(t, 3H), 1.70(m, 2H), 2.60(q, 2H), 4.03(t, 2H),4.51– 4.55(t, 2H), 5.20(dd, 2H), 8.29, 8.30(m, 1H). |
| 34 | 0.95–0.99(m, 6H), 1.41(m, 4H), 1.70(m, 2H), 1.81(m, 2H), 4.05 (t, 2H), 4.44–4.48(t, 2H), 7.40(d, 1H), 7.58(d, 1H), 8.13(s, 1H). |
| 38 | 0.94–1.03(2-t, 6H), 1.40(m, 2H), 1.48(m, 2H), 1.65(m, 2H), 1.80(m, 2H), 4.10(t, 2H), 4.47(t, 2H), 7.34(d, 1H), 7.70(d, 1H), 8.29(s, 1H). |
| 43 | 2.22(s, 6H), 7.33(d, 1H), 7.71(d, 1H), 8.30(s, 1H). |
| 47 | 1.45(d, 3H), 7.30(d, 1H), 7.68(d, 1H), 8.29(s, 1H). |
| 48 | 7.31(d, 1H), 7.69(d, 1H), 8.30(s, 1H). |
| 63 | 0.88–0.92(m, 9H), 1.59(m, 4H), 1.75(m, 2H), 3.09–3.13(t, 4H), 4.08(t, 2H), 7.38(d, 1H), 7.70(d, 1H), 8.30(s, 1H). |
| 70 | 0.99(m, 6H), 1.44(m, 4H), 1.66(m, 2H), 3.53(q, 2H), 4.00(t, 2H), 4.49(s, 1H), 7.25(d, 1H), 7.61(d 1H), 8.10(s, 1H). |
| 72 | 8.40(s, 1H), 7.89(d, 1H), 7.10(d, 1H), 4.50(s, 1H), 4.0(t, 2H), 3.53(q, 2H), 1.68(m, 4H), 1.45(m, 4H), 0.96–1.01(m, 6H). |
| 73 | 8.40(s, 1H), 7.79(d, 1H), 7.10(d, 1H), 4.52(s, 1H), 4.0(t, 2H), 3.49(q, 2H), 1.70(m, 4H), 1.43(m, 2H), 0.96–1.02(m, 6H). |

Results for Tests A–E are given in Table 13. In the table, a rating of 100 indicates 100% disease control and a rating of 0 indicates no disease control (relative to the controls). "-"=not tested.

TABLE 13

| Cmpd No. | Test A$^1$ | Test B | Test C | Test D | Test E |
|---|---|---|---|---|---|
| 1 | 100 | 4 | 24 | 58 | 0 |
| 2 | 75 | 7 | 0 | 18 | 0 |
| 3 | 72 | 59 | 0 | 92 | 0 |
| 4 | 41 | 3 | 0 | 26 | 0 |
| 5 | 54 | 0 | 23 | 50 | 0 |
| 6 | 45 | 0 | 0 | 0 | 81 |
| 7 | 7 | 57 | 23 | 50 | 0 |
| 8 | 14 | 3 | 0 | 26 | 0 |
| 9 | 96 | 0 | 0 | 39 | 0 |
| 10 | 40 | 0 | 0 | 17 | 67 |
| 12 | 100 | 0 | 0 | 91 | 83 |
| 13 | 95$^2$ | 0 | 0 | 0 | 0 |
| 14 | 100 | 0 | 0 | 41 | 45 |
| 15 | 99$^3$ | 0 | 0 | 41 | 4 |
| 16 | 100$^3$ | 0 | 0 | 41 | 0 |
| 17 | 99$^3$ | 0 | 33 | 0 | 0 |
| 18 | 100$^3$ | 20 | 20 | 0 | 32 |
| 22 | 100 | 0 | 0 | 41 | 0 |
| 23 | 97 | 46 | 0 | 0 | 0 |
| 25 | 100$^3$ | 46 | 0 | 8 | 0 |
| 26 | — | 41 | 0 | 6 | 0 |
| 27 | 100 | 7 | 0 | 18 | 0 |
| 29 | 97 | 46 | 0 | 0 | 0 |
| 30 | 100$^3$ | 3 | 0 | 26 | 0 |
| 31 | 38 | 3 | 0 | 26 | 0 |
| 32 | 100$^3$ | 3 | 0 | 26 | 0 |
| 33 | 100 | 3 | 0 | 81 | 0 |
| 34 | 100$^3$ | 3 | 0 | 68 | 0 |
| 35 | 100$^3$ | 0 | 0 | 0 | 0 |
| 36 | 100$^3$ | 3 | 0 | 50 | 0 |
| 37 | 100$^3$ | 93 | 26 | 13 | 0 |
| 38 | 100$^3$ | 54 | 66 | 99 | 0 |
| 39 | 99$^3$ | 0 | 0 | 16 | 0 |
| 40 | 100$^3$ | 54 | 100 | 16 | 0 |
| 41 | 100 | 0 | 23 | 41 | 0 |
| 42 | — | 0 | 23 | 0 | 0 |
| 43 | 100$^3$ | 62 | 45 | 62 | 0 |
| 44 | 100$^3$ | 62 | 0 | 0 | 0 |
| 45 | 100$^3$ | 0 | 0 | 0 | 67 |
| 46 | 100$^3$ | 0 | 0 | 17 | 0 |
| 47 | 50$^1$ | 0 | 0 | 0 | 0 |
| 48 | 92$^3$ | 61 | 0 | 0 | 0 |
| 49 | 36 | 16 | 0 | 56 | 0 |
| 50 | 99$^3$ | 0 | 0 | 56 | 0 |
| 51 | 100$^3$ | 4 | 0 | 56 | 63 |
| 52 | 100$^3$ | 57 | 0 | 10 | 36 |
| 53 | 100$^3$ | 4 | 0 | 83 | 36 |
| 54 | 95 | 43 | 0 | 10 | 0 |
| 55 | 59$^3$ | 81 | 0 | 74 | 0 |
| 56 | 57$^3$ | 92 | 0 | 17 | 0 |
| 57 | 91 | 12 | 23 | 99 | 37 |
| 58 | 98 | — | — | — | — |

TABLE 13-continued

| Cmpd No. | Test A[1] | Test B | Test C | Test D | Test E |
|---|---|---|---|---|---|
| 59 | 100 | 56 | 0 | 8 | 0 |
| 60 | — | 0 | 0 | 7 | 0 |
| 61 | 100[3] | 15 | 0 | 33 | 65 |
| 62 | 99 | 83 | 19 | 98 | 28 |
| 63 | 97 | 0 | 42 | 100 | 28 |
| 64 | 100[3] | 76 | 43 | 0 | 0 |
| 65 | 100[3] | 23[2] | 0 | 96 | 44 |
| 66 | 99 | 0 | 0 | 0 | 0 |
| 67 | 89[3] | 7 | 0 | 18 | 0 |
| 68 | 100[3] | 0 | 26 | 13 | 0 |
| 69 | 94 | 79 | 80 | 89 | 0 |
| 70 | 97 | 63 | 0 | 100 | 0 |
| 71 | 100[3] | 57 | 0 | 56 | 63 |
| 72 | 100[3] | 4 | 0 | 91 | 63 |
| 73 | 100 | 57 | 0 | 72 | 63 |
| 76 | 99[3] | 16 | 21 | 9 | 0 |
| 77 | 99 | 52 | 44 | 100 | 68 |
| 79 | 97[2] | 6 | 0 | 39 | 0 |
| 80 | 100[3] | 57 | 0 | 56 | 0 |

[1]Test was run at 10 ppm unless otherwise indicated.
[2]Test was run at 40 ppm.
[3]Test was run at 2 ppm.

We claim:

1. A compound of Formula I, II, or III

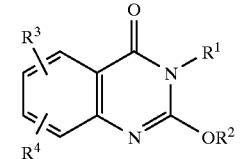

(I)

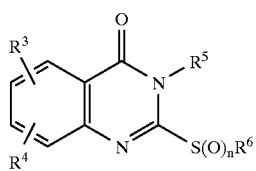

(II)

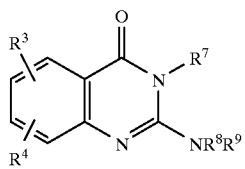

(III)

wherein:

n is 0, 1 or 2;

Q is independently O or S;

$R^1$ is $C_3$–$C_{10}$ alkyl; $C_3$–$C_5$ cycloalkyl; $C_4$–$C_{10}$ alkenyl; $C_4$–$C_{10}$ alkynyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_5$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$, nitro, cyano, or phenyl optionally substituted with $R^{14}$, $R^{15}$, and $R^{16}$; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{11}R^{12}$; or pyridyl, furanyl, thienyl, naphthyl, benzofuranyl, benzothienyl, or quinolinyl each optionally substituted with $R^{14}$, $R^{15}$, and $R^{16}$;

$R^2$ is $C_3$–$C_{10}$ alkyl; $C_6$–$C_7$ cycloalkyl; $C_3$–$C_{10}$ alkenyl; $C_3$–$C_{10}$ alkynyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_3$–$C_{10}$ cyanoalkyl; $C_2$–$C_{10}$ nitroalkyl; $C_1$–$C_{10}$ alkyl substituted with $CO_2R^{11}$, $NR^{11}R^{12}$, or phenyl optionally substituted with $R^{13}$, $R^{15}$, and $R^{16}$; phenyl optionally substituted with $R^{13}$, $R^{15}$, and $R^{16}$; —N=$CR^{11}R^{11}$; or —$NR^{11}R^{12}$; or $R^1$ and $R^2$ are taken together to form —$CH_2(CH_2)_m$ $CH_2$—;

m is 1–4;

$R^3$ is $C_3$–$C_8$ cycloalkyl; $C_2$–$C_8$ alkenyl; $C_2$–$C_8$ alkynyl; $C_1$–$C_8$ haloalkyl; $C_3$–$C_8$ haloalkenyl; $C_3$–$C_8$ haloalkynyl; $C_1$–$C_8$ haloalkoxy; $C_3$–$C_8$ alkenyloxy; $C_3$–$C_8$ alkynyloxy; $C_1$–$C_8$ alkylthio; $C_3$–$C_8$ alkenylthio; $C_3$–$C_8$ alkynylthio; $C_1$–$C_8$ alkylsulfinyl; $C_1$–$C_8$ alkylsulfonyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ cycloalkylalkyl; $C_3$–$C_8$ trialkylsilyl; $NR^{11}R^{12}$; $C_5$–$C_8$ trialkylsilylalkynyl; or phenyl optionally substituted with at least one $R^{13}$;

$R^4$ is hydrogen; halogen; $C_1$–$C_4$ alkyl; $C_1$–$C_4$ haloalkyl; $C_1$–$C_4$ alkoxy; or $C_1$–$C_4$ haloalkoxy;

$R^5$ is $C_3$–$C_5$ alkyl; $C_7$–$C_{10}$ alkyl; $C_4$–$C_7$ alkenyl; $C_3$–$C_5$ alkynyl; $C_1$–$C_{10}$ haloalkyl; $C_5$–$C_{10}$ haloalkenyl; $C_3$–$C_{10}$ haloalkynyl; $C_2$–$C_{10}$ alkoxyalkyl other than methoxypropyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$, nitro, or phenyl optionally substituted with at least one of $R^{14}$, $R^{15}$, and $R^{16}$; $C_2$–$C_{10}$ alkyl substituted with cyano; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{11}R^{12}$; or phenyl, furanyl, thienyl, naphthyl, benzofuranyl, or benzothienyl each optionally substituted with $R^{14}$, $R^{15}$, and $R^{16}$;

$R^6$ is $C_3$–$C_{10}$ alkyl; $C_3$–$C_7$ alkenyl; $C_3$–$C_{10}$ alkynyl; $C_1$–$C_{10}$ haloalkyl; $C_3$–$C_{10}$ haloalkenyl; $C_3$–$C_{10}$ haloalkynyl; $C_3$–$C_{10}$ alkoxyalkyl other than propoxymethyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_5$–$C_{10}$ cyanoalkyl; $C_2$–$C_{10}$ nitroalkyl; or $C_3$–$C_{10}$ alkyl substituted with $CO_2R^{11}$, $NR^{11}R^{12}$, or phenyl optionally substituted with $R^{13}$, $R^{15}$, and $R^{16}$; or phenyl optionally substituted with $R^{13}$, $R^{15}$, and $R^{16}$; or $R^5$ and $R^6$ are taken together to form —$CH_2(CH_2)_m$ $CH_2$—;

$R^7$ is $C_3$–$C_{10}$ alkyl; $C_3$–$C_7$ cycloalkyl; $C_4$–$C_7$ alkenyl; propynyl; $C_5$–$C_{10}$ alkynyl; $C_2$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R^{12}$ or nitro; $C_2$–$C_{10}$ alkyl substituted with cyano; $C_1$–$C_{10}$ alkoxy; $C_1$–$C_{10}$ haloalkoxy; $C_1$–$C_{10}$ alkylthio; $C_1$–$C_{10}$ haloalkylthio; $NR^{12}R^{17}$; or phenyl, pyridyl, furanyl, thienyl, naphthyl, benzofuranyl, benzothienyl, or quinolinyl each optionally substituted with $R^{14}$, $R^{15}$, and $R^{16}$;

$R^8$ is $C_1$–$C_4$ alkyl; or —C(=O)$R^{10}$;

$R^9$ is $C_2$–$C_{10}$ alkyl; $C_3$–$C_7$ cycloalkyl; $C_3$–$C_{10}$ alkenyl; $C_3$–$C_{10}$ alkynyl; $C_3$–$C_{10}$ haloalkyl; $C_3$–$C_{10}$ haloalkenyl; $C_3$–$C_{10}$ haloalkynyl; $C_3$–$C_{10}$ alkoxyalkyl other than butoxyethyl; $C_2$–$C_{10}$ alkylthioalkyl; $C_2$–$C_{10}$ alkylsulfinylalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ (cycloalkyl)oxyalkyl; $C_4$–$C_{10}$ alkenylthioalkyl; $C_4$–$C_{10}$ alkynylthioalkyl; $C_6$–$C_{10}$ (cycloalkyl)thioalkyl; $C_2$–$C_{10}$ haloalkoxyalkyl; $C_4$–$C_{10}$ haloalkenyloxyalkyl; $C_4$–$C_{10}$ haloalkynyloxyalkyl; $C_4$–$C_{10}$ alkoxyalkenyl; $C_4$–$C_{10}$ alkoxyalkynyl; $C_4$–$C_{10}$ alkylthioalkenyl; $C_4$–$C_{10}$ alkylthioalkynyl; $C_4$–$C_{10}$ trialkylsilylalkyl; $C_1$–$C_{10}$ alkyl substituted with $NR^{11}R_{12}$; $C_4$–$C_{10}$ cyanoalkyl; $C_2$–$C_{10}$ nitroalkyl; $C_1$–$C_8$ alkyl substituted with $CO_2R^{11}$; pyridyl, furanyl, thienyl, or naphthyl each optionally substituted with $R^{14}$, $R^{15}$, and $R^{16}$; —N=$CR^{11}R^{11}$; —$NR^{12}R^{17}$; —$OR_{12}$; or —NC(=Q)$NR^{11}R^{12}$; or $R^3$ and $R^4$ are both iodine and $R^9$ is phenyl optionally substituted with $R^{14}$, $R^{15}$, and $R^{16}$; or $R^7$ and $R^9$ are taken together to form —$CH_2(CH_2)_m$ $CH_2$—;

$R^{10}$ is hydrogen; $C_1$–$C_4$ alkyl; $C_1$–$C_4$ alkoxy; or $NR^{11}R^{12}$;

$R^{11}$ is independently hydrogen; $C_1$–$C_4$ alkyl; or phenyl optionally substituted with at least one $R^{13}$;

$R^{12}$ is independently hydrogen; $C_1$–$C_8$ alkyl; or phenyl optionally substituted with at least one $R^{13}$; or $R^{11}$ and $R^{12}$ are taken together to form —$CH_2CH_2CH_2CH_2$—, —$CH_2(CH_2)_3CH_2$—, —$CH_2CH_2OCH_2CH_2$—, —$CH_2CH(Me)CH_2CH(Me)CH_2$—, or —$CH_2CH(Me)OCH(Me)CH_2$—;

$R^{13}$ is independently halogen; $C_1$–$C_4$ alkyl; $C_1$–$C_4$ alkoxy; $C_1$–$C_4$ haloalkyl; nitro; or cyano;

$R^{14}$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R^{13}$; cyano; nitro; $C_1$–$C_6$ haloalkoxy; $C_1$–$C_6$ haloalkylthio; $C_2$–$C_6$ alkenyl; $C_2$–$C_6$ haloalkenyl; acetyl; $CO_2Me$; or $N(C_1$–$C_2$ alkyl$)_2$;

$R^{15}$ is independently methyl; ethyl; methoxy; methylthio; halogen; or trifluoromethyl;

$R^{16}$ is independently halogen; and $R^{17}$ is independently $C_1$–$C_8$ alkyl; or phenyl optionally substituted with at least one $R^{13}$; or an N-oxide or agriculturally-suitable salt thereof.

2. A compound of Formula I of claim 1 wherein:

Q is O;

$R^1$ is $C_3$–$C_8$ alkyl; $C_4$–$C_8$ alkenyl; $C_4$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_5$–$C_8$ cycloalkylalkyl; $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or pyridyl, furanyl, or thienyl each optionally substituted with $R^{14}$ and $R^{15}$;

$R^2$ is $C_3$–$C_8$ alkyl; $C_3$–$C_8$ alkenyl; $C_3$–$C_8$ alkynyl; $C_1$–$C_8$ haloalkyl; $C_3$–$C_8$ haloalkenyl; $C_3$–$C_8$ alkoxyalkyl; $C_2$–$C_8$ alkylthioalkyl; $C_4$–$C_8$ cycloalkylalkyl; $C_3$–$C_8$ cyanoalkyl; $C_4$–$C_8$ alkenyloxyalkyl; or phenyl optionally substituted with $R^{13}$;

$R^3$ is $C_2$–$C_8$ alkynyl; $C_3$–$C_8$ cycloalkyl; $C_1$–$C_8$ haloalkyl; $C_1$–$C_8$ haloalkoxy; $C_1$–$C_8$ alkylthio; $C_1$–$C_8$ alkylsulfonyl; $C_2$–$C_8$ alkoxyalkyl; $C_2$–$C_8$ alkylthioalkyl; $C_4$–$C_8$ cycloalkylalkyl; or $C_5$–$C_8$ trialkylsilylalkynyl; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

3. A compound of Formula II of claim 1 wherein:

Q is O;

n is 0;

$R^3$ is $C_2$–$C_8$ alkynyl; $C_3$–$C_8$ cycloalkyl; $C_1$–$C_8$ haloalkyl; $C_1$–$C_8$ haloalkoxy; $C_1$–$C_8$ alkylthio; $C_1$–$C_8$ alkylsulfonyl; $C_2$–$C_8$ alkoxyalkyl; $C_2$–$C_8$ alkylthioalkyl; $C_4$–$C_8$ cycloalkylalkyl; or $C_5$–$C_8$ trialkylsilylalkynyl;

$R^5$ is $C_3$–$C_5$ alkyl; $C_4$–$C_7$ alkenyl; $C_3$–$C_5$ alkynyl; $C_1$–$C_8$ haloalkyl; $C_5$–$C_8$ haloalkenyl; $C_2$–$C_8$ alkoxyalkyl other than methoxypropyl; $C_2$–$C_8$ alkylthioalkyl; $C_4$–$C_8$ cycloalkylalkyl; $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or phenyl, furanyl, or thienyl each optionally substituted with $R^{14}$ and $R^{15}$;

$R^6$ is $C_3$–$C_8$ alkyl; $C_3$–$C_7$ alkenyl; $C_3$–$C_8$ alkynyl; $C_1$–$C_8$ haloalkyl; $C_3$–$C_8$ haloalkenyl; $C_3$–$C_8$ alkoxyalkyl other than propoxymethyl; $C_2$–$C_8$ alkylthioalkyl; $C_4$–$C_8$ cycloalkylalkyl; $C_5$–$C_8$ cyanoalkyl; $C_4$–$C_8$ alkenyloxyalkyl; phenyl optionally substituted with $R^{13}$; or $C_3$–$C_5$ alkyl substituted with phenyl optionally substituted with $R^{13}$ and $R^{15}$; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

4. A compound of Formula III of claim 1 wherein:

Q is O;

$R^3$ is $C_2$–$C_8$ alkynyl; $C_3$–$C_8$ cycloalkyl; $C_1$–$C_8$ haloalkyl; $C_1$–$C_8$ haloalkoxy; $C_1$–$C_8$ alkylthio; $C_1$–$C_8$ alkylsulfonyl; $C_2$–$C_8$ alkoxyalkyl; $C_2$–$C_8$ alkylthioalkyl; $C_4$–$C_8$ cycloalkylalkyl; or $C_5$–$C_8$ trialkylsilylalkynyl;

$R^7$ is $C_3$–$C_8$ alkyl; $C_4$–$C_7$ alkenyl; propynyl; $C_2$–$C_8$ haloalkyl; $C_3$–$C_8$ haloalkenyl; $C_2$–$C_8$ alkoxyalkyl; $C_2$–$C_8$ alkylthioalkyl; $C_2$–$C_8$ alkyl substituted with cyano; $C_1$–$C_8$ alkoxy; $C_1$–$C_8$ haloalkoxy; $C_1$–$C_8$ alkylthio; or $C_4$–$C_8$ alkenyloxyalkyl; or phenyl, pyridyl, furanyl, or thienyl each optionally substituted with $R^{14}$ and $R_{15}$;

$R_9$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; $C_2$–$C_8$ alkylthioalkyl; $C_4$–$C_8$ cycloalkylalkyl; $C_4$–$C_8$ cyanoalkyl; $C_4$–$C_8$ alkenyloxyalkyl; —$NR^{12}R^{17}$; or $R^3$ and $R^4$ are both iodine and $R^9$ is phenyl optionally substituted with $R^{14}$ and $R^{15}$; and $R^{14}$ is methyl; ethyl; methoxy; ethoxy; $C_1$–$C_2$ haloalkyl; halogen; acetylenyl; propargyl; methylthio; ethylthio; cyano; nitro; $C_1$–$C_2$ haloalkoxy; vinyl; allyl; acetyl; $CO_2Me$; or $N(C_1$–$C_2$ alkyl$)_2$.

5. A compound of claim 2 wherein:

$R^1$ is $C_3$–$C_8$ alkyl; $C_4$–$C_8$ alkenyl; $C_4$–$C_8$ alkynyl; $C_3$–$C_8$ haloalkyl; $C_3$–$C_8$ haloalkenyl; $C_3$–$C_8$ alkoxyalkyl; or thienyl optionally substituted with at least one of $R^{14}$ and $R^{15}$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^{13}$;

$R^3$ is $C_1$–$C_4$ haloalkyl; $C_1$–$C_4$ haloalkoxy; acetylenyl; or trimethylsilylacetylenyl; and $R^{14}$ is methyl; ethyl; methoxy; methylthio; halogen; trifluoromethyl; or $N(C_1$–$C_2$ alkyl$)_2$.

6. A compound of claim 3 wherein:

$R^3$ is $C_1$–$C_4$ haloalkyl; $C_1$–$C_4$ haloalkoxy; acetylenyl; or trimethylsilylacetylenyl;

$R^5$ is $C_3$–$C_5$ alkyl; $C_4$–$C_7$ alkenyl; $C_3$–$C_5$ alkynyl; $C_3$–$C_8$ haloalkyl; $C_5$–$C_8$ haloalkenyl; $C_3$–$C_8$ alkoxyalkyl; or phenyl or thienyl each optionally substituted with $R^{14}$ and $R^{15}$;

$R^6$ is $C_3$–$C_8$ alkyl; $C_3$–$C_7$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^{13}$; and $R^{14}$ is methyl; ethyl; methoxy; methylthio; halogen; trifluoromethyl; or $N(C_1$–$C_2$ alkyl$)_2$.

7. A compound of claim 4 wherein:

$R^3$ is $C_1$–$C_4$ haloalkyl; $C_1$–$C_4$ haloalkoxy; acetylenyl; or trimethylsilylacetylenyl;

$R^7$ is $C_3$–$C_8$ alkyl; $C_4$–$C_7$ alkenyl; propynyl; $C_3$–$C_8$ haloalkyl; $C_3$–$C_8$ haloalkenyl; $C_3$–$C_8$ alkoxy; $C_3$–$C_8$ alkoxyalkyl; or phenyl or thienyl each optionally substituted with $R^{14}$ and $R^{15}$;

$R^9$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; —$NR^{12}R^{17}$; or $R^3$ and $R^4$ are both iodine and $R^9$ is phenyl optionally substituted with $R^{14}$ and $R^{15}$; and $R^{14}$ is methyl; ethyl; methoxy; methylthio; halogen; trifluoromethyl; or $N(C_1$–$C_2$ alkyl$)_2$.

8. A method for controlling plant diseases caused by fungal plant pathogens, comprising applying to the plant or portion thereof to be protected, to the media in which the plant to be protected is growing, or to the plant seed or seedling to be protected an effective amount of the compound of claim 1.

9. A fungicidal composition comprising an effective amount of the compound of claim 1 and at least one of (a) a surfactant, (b) an organic solvent, and (c) at least one solid or liquid diluent.

10. A method for controlling wheat powdery mildew comprising applying to the plant or portion thereof to be protected, to the media in which the plant to be protected is growing, or to the plant seed or seedling to be protected an effective amount of the compound of claim 1.

* * * * *